US007820210B2

(12) United States Patent
Vail, III et al.

(10) Patent No.: US 7,820,210 B2
(45) Date of Patent: Oct. 26, 2010

(54) METHODS AND APPARATUS TO PREVENT, TREAT, AND CURE THE SYMPTOMS OF NAUSEA CAUSED BY CHEMOTHERAPY TREATMENTS OF HUMAN CANCERS

(75) Inventors: William Banning Vail, III, Bothell, WA (US); Marilyn L. Vail, Bothell, WA (US)

(73) Assignee: Inhalation, Inc., Snohomish, WA (US)

( * ) Notice: Subject to any disclaimer, the term of this patent is extended or adjusted under 35 U.S.C. 154(b) by 395 days.

(21) Appl. No.: 12/077,467

(22) Filed: Mar. 18, 2008

(65) Prior Publication Data

US 2008/0187609 A1 Aug. 7, 2008

Related U.S. Application Data

(63) Continuation-in-part of application No. 10/998,343, filed on Nov. 27, 2004, now Pat. No. 7,344,740, which is a continuation-in-part of application No. 10/924,224, filed on Aug. 23, 2004, now abandoned, which is a continuation-in-part of application No. 10/429,077, filed on May 2, 2003, now Pat. No. 7,048,953, which is a continuation-in-part of application No. 10/269,891, filed on Oct. 12, 2002, now abandoned, which is a continuation-in-part of application No. 10/241,441, filed on Sep. 9, 2002, now Pat. No. 7,150,888, which is a continuation-in-part of application No. 09/542,703, filed on Apr. 3, 2000, now Pat. No. 6,447,816.

(51) Int. Cl.
*A61K 36/53* (2006.01)
*A61P 1/08* (2006.01)

(52) U.S. Cl. ...................................... 424/747; 514/872

(58) Field of Classification Search ....................... None
See application file for complete search history.

(56) References Cited

U.S. PATENT DOCUMENTS 7,344,740 B2 * 3/2008 Vail et al.

* cited by examiner

*Primary Examiner*—Michele C. Flood

(57) ABSTRACT

Methods and apparatus are provided to prevent, treat, and cure chemotherapy induced nausea in human beings. The inhalation of an effective amount of vaporized essential oil from *Mentha piperita* (peppermint oil) has been shown in practice to prevent, treat, and cure chemotherapy induced nausea. A simple hand-held apparatus provides the vapors to be inhaled through the nostril to prevent, treat, and cure chemotherapy induced nausea.

2 Claims, 13 Drawing Sheets

METHODS AND APPARATUS TO PREVENT, TREAT, AND CURE THE SYMPTOMS OF NAUSEA CAUSED BY CHEMOTHERAPY TREATMENTS OF HUMAN CANCERS

CROSS-REFERENCES TO RELATED APPLICATIONS

This application is a Continuation-in-Part Application of Ser. No. 10/998,343, having the Filing Date of Nov. 27, 2004, now U.S. Pat. No. 7,344,740 that is entitled "Methods and Apparatus to Prevent, Treat, and Cure the Symptoms of Nausea Caused by Chemotherapy Treatments of Human Cancers", that was Published as US 2005-0158411 A1 on the Publication Date of Jul. 21, 2005, entire copies of which documents are incorporated herein by reference.

Ser. No. 10/998,343 is a Continuation-in-Part Application of Ser. No. 10/924,224, having the Filing Date of Aug. 23, 2004, that is entitled "Methods and Apparatus to Inhale Vapors from Coffee Beans to Stimulate the Human Body", now abandoned, an entire copy of which is incorporated herein by reference.

Ser. No. 10/924,224 is a Continuation-in-Part Application of Ser. No. 10/429,077, having the Filing Date of May 2, 2003, that is entitled "Methods and Apparatus to Prevent, Treat and Cure Infections of the Human Respiratory System by Pathogens Causing Severe Acute Respiratory Syndrome (SARS)", which Application was Published as US 2004-0009245 A1 on the date of Jan. 15, 2004, and which application issued as U.S. Pat. No. 7,048,953 B2 on the date of May 23, 2006, entire copies of which documents are incorporated herein by reference.

Ser. No. 10/429,077 is a Continuation-in-Part Application of application Ser. No. 10/269,891, having the Filing Date of Oct. 12, 2002, now abandoned that is entitled "Methods and Apparatus to Prevent, Treat and Cure Infections of the Human Respiratory System from Inhaled Anthrax, Smallpox, Botulism, Plague, Tularemia, Hemorrhagic Fever Viruses, Tuberculosis and Other Inhaled Bioterrorism Pathogens", an entire copy of which is incorporated herein by reference.

Ser. No. 10/269,891 is a Continuation-in-Part Application of Ser. No. 10/241,441, having the Filing Date of Sep. 9, 2002, that is entitled "Methods and Apparatus to Prevent Colds, Flus, Tuberculosis and Opportunistic Infections of the Human Respiratory System of Individuals Having Cystic Fibrosis", which application issued as U.S. Pat. No. 7,150,888 B1 on the date of Dec. 19, 2006, entire copies of which documents are incorporated herein by reference.

Ser. No. 10/241,441 is a Continuation-in-Part Application of Ser. No. 09/542,703, having the Filing Date of Apr. 3, 2000 that is entitled "Methods and Apparatus to Prevent Colds, Flus, and Infections of the Human Respiratory System", that issued as U.S. Pat. No. 6,447,816 B1 on the date of Sep. 10, 2002, an entire copy of which is incorporated herein by reference.

This application relates to Provisional Patent Application No. 60/328,912 filed on Oct. 12, 2001 that is entitled "Methods and Apparatus to Prevent Infections of the Human Respiratory System from Inhaled Anthrax, Smallpox, Botulism, Plague, Tularemia, Tuberculosis and Other Inhaled Bioterrorism Pathogens". An entire copy of Provisional Patent Application No. 60/328,912 is incorporated herein by reference.

This application also relates to Provisional Patent Application No. 60/377,177 filed on May 2, 2002 that is entitled "Methods and Apparatus to Prevent, Treat, and Cure Infections of the Human Respiratory System Including the Sinus Cavities, the Nasal Cavities, and the Throat". An entire copy of Provisional Patent Application No. 60/377,177 is incorporated herein by reference.

This application further relates to Provisional Patent Application No. 60/449,379 filed on Feb. 21, 2003 that is entitled "Hand Held Inhalers". An entire copy of Provisional Patent Application No. 60/449,379 is incorporated herein by reference.

This application also relates to Provisional Patent Application No. 60/457,085 filed on Mar. 24, 2003 that is entitled 'Methods and Apparatus to Prevent, Treat, and Cure Infections of Severe Acute Respiratory Syndrome ("SARS")'. An entire copy of Provisional Patent Application No. 60/457,085 is incorporated herein by reference.

This application further relates to Provisional Patent Application No. 60/457,849 filed on Mar. 26, 2003 that is entitled 'Methods and Apparatus to Prevent, Treat, and Cure Severe Acute Respiratory Syndrome ("SARS") Caused by the Infection of One or More Coronaviruses in the Human Respiratory System'. An entire copy of Provisional Patent Application No. 60/457,849 is incorporated herein by reference.

This application also relates to Provisional Patent Application No. 60/460,985 filed on Apr. 7, 2003 that is entitled 'Methods and Apparatus to Prevent, Treat, and Cure Severe Acute Respiratory Syndrome ("SARS") Caused by the Infection of Two or More Associated Viruses, Bacteria and Fungi". An entire copy of Provisional Patent Application No. 60/460,985 is incorporated herein by reference.

This application further relates to Provisional Patent Application No. 60/497,381 filed on Aug. 22, 2003 that is entitled "Methods and Apparatus to Inhale Vapors from Coffee Beans to Stimulate the Human Body". An entire copy of Provisional Patent Application No. 60/497,381 is incorporated herein by reference.

This application also relates to Provisional Patent Application No. 60/520,382 filed on Nov. 15, 2003 that is entitled "Methods and Apparatus to User Botanical Essential Oils to Sexually Stimulate the Human Female and to Revitalize the Tissues in the Vagina of the Post-Menopausal Human Female". An entire copy of Provisional Patent Application No. 60/520,382 is incorporated herein by reference.

This application also relates to Provisional Patent Application No. 60/527,933 filed on Dec. 8, 2003 that is entitled "Methods and Apparatus to Prevent, Treat, and Cure the Symptoms of Nausea Caused by Chemotherapy Treatments of Human Cancers." An entire copy of Provisional Patent Application No. 60/527,933 is incorporated herein by reference.

Applicant claims priority from the above U.S. patent application Ser. No. 10/998,343 having the Filing Date of Nov. 27, 2004. Applicant also claims priority from the above U.S. patent application Ser. No. 10/924,224 having the Filing Date of Aug. 23, 2004. Applicant also claims priority from the above U.S. patent application Ser. No. 10/429,077 having the Filing Date of May 2, 2003. Applicant also claims priority from the above U.S. patent application Ser. No. 10/269,891 having the Filing Date of Oct. 12, 2002. Applicant also claims priority from the above U.S. patent application Ser. No. 10/241,441, having the Filing Date of Sep. 9, 2002. Applicant also claims priority from U.S. patent application Ser. No. 09/542,703 having the Filing Date of Apr. 3, 2000.

Applicant also claims any priority from Provisional Patent Application No. 60/328,912 having the Filing Date Oct. 12, 2001. (now expired) Applicant further claims any priority from Provisional Patent Application No. 60/377,177 having the Filing Date May 2, 2002. (now expired) Applicant also claims any priority from Provisional Patent Application No.

60/449,379 having the Filing Date of Feb. 21, 2003. (now expired) Applicant further claims any priority from Provisional Patent Application No. 60/457,085 having the Filing Date of Mar. 24, 2003. (now expired) Applicant also claims any priority from Provisional Patent Application No. 60/457,849 having the Filing Date of Mar. 26, 2003. (now expired) Applicant further claims any priority from Provisional Patent Application No. 60/460,985 having the Filing Date of Apr. 7, 2003. (now expired) Applicant further claims any priority from Provisional Patent Application No. 60/497,381 having the Filing Date of Aug. 22, 2003. (now expired) Applicant further claims any priority from Provisional Patent Application No. 60/520,382 having the Filing Date of Nov. 15, 2003. (now expired) Applicant also claims any priority from Provisional Patent Application No. 60/527,933 having the Filing Date of Dec. 8, 2003. (now expired)

This application is related to U.S. Disclosure Document No. 520,804 that has the Filing Date of Oct. 29, 2002 that is entitled "Additional Methods of Using the Inhalers for Sports Performance, to Enhance memory, To Prevent, Treat or Cure PMS, Hot Flashes, and Night Sweats, to Treat or Reduce Stress, for Dietary Control, as Aphrodisiacs, Antidepressants, and for Other Purposes", an entire copy of which is incorporated herein by reference.

This application is related to U.S. Disclosure Document No. 528,070 that has the Filing Date of Mar. 17, 2003 that is entitled 'Methods and Apparatus to Prevent, Treat, and Cure Infections of Severe Acute Respiratory Syndrome ("SARS") ', an entire copy of which is incorporated herein by reference.

BACKGROUND OF THE INVENTION

One of the inventors has poor respiratory health, has had repeated bouts with pneumonia, colds, flu, asthma, and has been recently diagnosed with the initial stages of emphysema—despite all that modern medicine has had to offer. This first inventor also comes from a family known for a long history of respiratory problems. Therefore, the inventors decided to look beyond conventional "modern medicine" to help the first inventor, and as a result, have conceived methods to substantially prevent colds, flus, and infections of the human respiratory system. These methods include the inhalation of the vapors from *eucalyptus* oil and/or tea tree oil that are theorized to form a protective, and infection-preventing, thin layer within the entire respiratory system, including the lungs, bronchial tubes, and the nasal cavities. This thin layer maintains its anti-pathogenic properties for a period of time following the inhalation of the vapors for at least one-half hour, and perhaps longer. This thin anti-pathogenic layer substantially prevents the initial infection of colds, flus, and other pathogens for a period of time following inhalation. The inventors also propose the prophylactic use of inhaled *eucalyptus* oil and/or tea tree oil to prevent additional pathogenic infections such as tuberculosis, which is becoming a major health problem in the United States. The inventors further propose the prophylactic use of inhaled *eucalyptus* oil and/or tea tree oil to prevent opportunistic infections of the human respiratory system of individuals having cystic fibrosis.

1. Field of the Invention

The field of invention relates to the prevention of colds, flus, and other diseases caused by pathogens within the respiratory system of human beings by the inhalation of vapors from highly volatile essential oils such as *eucalyptus* oil and/or tea tree oil. Following the inhalation of the vapors, a thin anti-pathogenic layer is formed in the respiratory system that protects against infection for a certain duration of time following inhalation. The field of invention further relates to the inhalation of vapors from coffee beans within a hand-held apparatus to stimulate the human body. The field of invention also relates to the inhalation of vapors from *Mentha piperita* to prevent, treat, and cure chemotherapy induced nausea.

2. Description of the Prior Art

While certain medical uses for *eucalyptus* oil and tea tree oil have been previously disclosed, to the inventor's best knowledge, none of those previously disclosed methods have suggested, or proposed, that the periodic inhalation of vapors from *eucalyptus* oil and/or tea tree oil may be used as prophylactic agents to substantially prevent infection of colds, flus, and other pathogens within the respiratory system of human beings for a duration of time following that inhalation. AFTER the infection of human beings with certain pathogens, previous inhalation therapies have suggested using *eucalyptus* oil and or tea tree oil to aid in the recovery from certain respiratory diseases. However, none of these previous methods have suggested using *eucalyptus* oil and/or tea tree oil vapors as prophylactic agents to routinely and substantially PREVENT the initial infection of pathogens for a duration of time following their inhalation as a primary method of preventing disease.

SUMMARY OF THE INVENTION

An object of the invention to provide methods and hand-held apparatus to inhale vapors from *Mentha piperita* to prevent, treat, or cure chemotherapy induced nausea.

DESCRIPTION OF THE PREFERRED EMBODIMENTS

Figure 1:
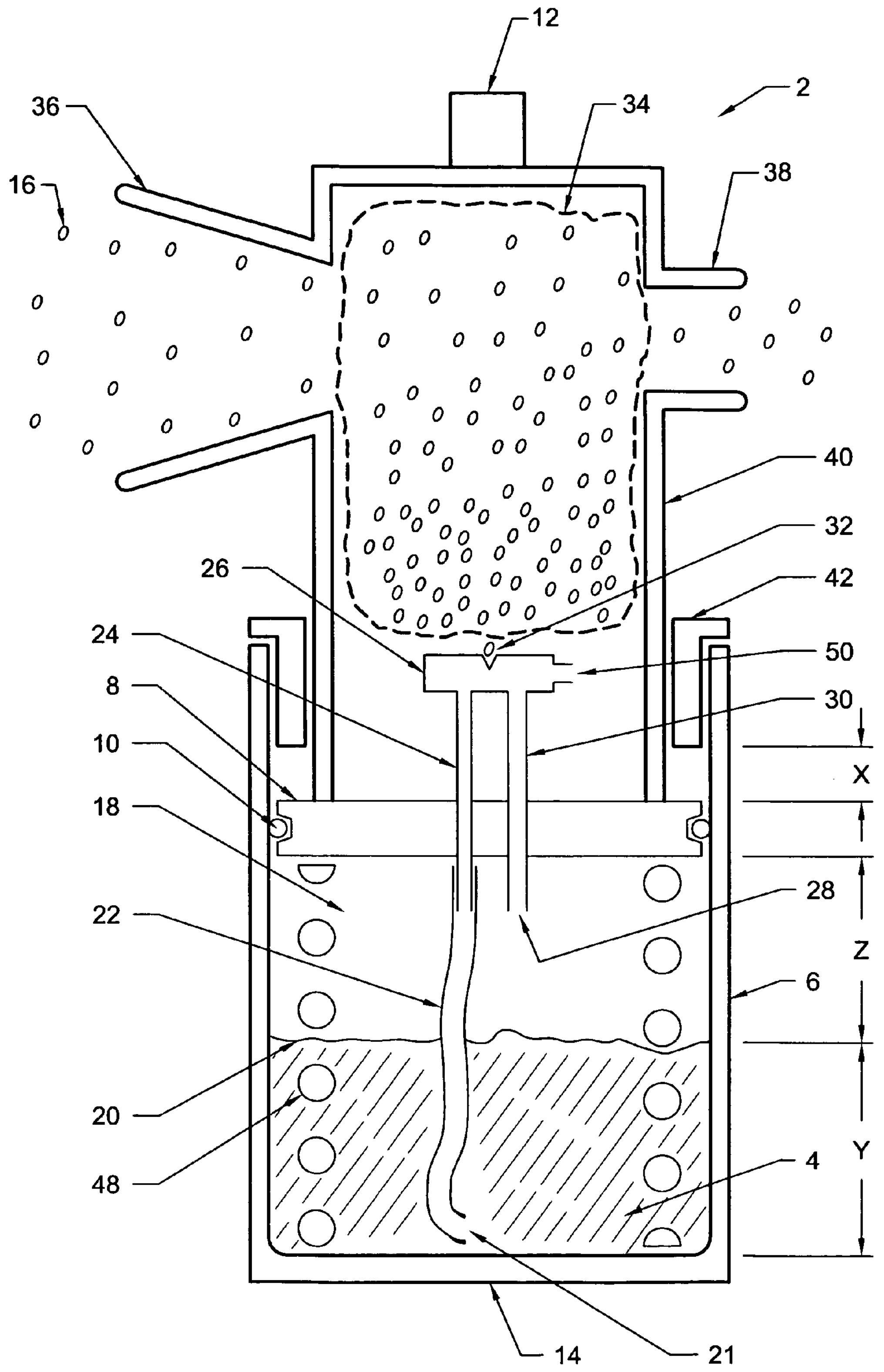
FIG. 1 shows a section view of a hand-held atomizer apparatus to produce vapors from *eucalyptus* oil and/or tea tree oil or from other mixtures of essential oils for inhalation.

Following a business trip to Houston during April of 1998, the first inventor, W. Banning Vail, Ph.D., returned to Seattle and caught a dreadful form of flu. During this severe illness, the first inventor spent several weeks gasping for breath and nearly died. After several trips to a pulmonary specialist, it was found that about ⅓ of the first inventor's lung capacity had been "eaten up" by some sort of infectious agent. Therefore, the first inventor was diagnosed with a form of emphysema.

The physician further informed the first inventor that if one more such infectious episode should occur, and should that episode result in another ⅙ or more of the first inventor's lung capacity being "eaten up" by an infectious agent, then the first inventor would thereafter become a good candidate for use of oxygen tanks. Further, the first inventor was also diagnosed with asthma. The physician provided additional warnings of potential disaster in light of the first inventor's many childhood bouts with pneumonia that left scars on the lungs. Such warnings were also compounded by the first inventor's stupid habit of smoking, which he quit some 20 years ago.

The first inventor's father, William Banning Vail, Jr., had emphysema, and had used oxygen tanks for perhaps five years. Accordingly, the first inventor feared emphysema and the use of oxygen tanks. The terms such as "emphysema", "asthma", and related diseases are defined and described in Weinstein, 1988, an entire copy of which is incorporated herein by reference. The clinical manifestations of emphysema, asthma, and other respiratory infections are defined and described in Luckmann, 1997, an entire copy of which is incorporated herein by reference.

For many years, it seems almost every time that the first inventor had taken an airplane flight, or had otherwise gone into a public place with a large number of people, he had often caught a cold, a flu, or some other "bug". The terms such as "cold", "flu", "infectious disease", "pathogen" "pathogens", "pathogenesis", "pathologic microorganisms", etc., are defined in Anderson, et al., 1994, an entire copy of which is incorporated herein by reference. Here, colds include diseases caused by any strain of a rhinovirus. Here, flus include diseases caused by any type of influenza, including those of the respiratory system. Therefore, the first inventor came to fear airplane flights, being in places with many people, etc. because of fear of being infected again with pathogens that could possible result in death by terminal emphysema.

In Anderson, et. al, 1994, on page 808, the term "risk for infection" is defined as "a state in which an individual is at increased risk for being invaded by pathogenic organisms". Anderson, et. al, 1994, page 808, further states: "Risk factors include inadequate primary defenses, such as broken skin, traumatized tissue, decrease in ciliary action, . . . , tissue destruction, . . . ".

Luckmann, 1997, page 868, also states under the topic of "Nonspecific Body Defenses Against Infection", and under "1. Physical barriers" the following:

"a. Physical, or anatomic, barriers are the 1st line of defense against infection." and "b. Physical barriers include intact skin and mucous membranes lining the respiratory, gastrointestinal and genitourinary tracts."

Therefore, Luckmann, 1997 specifically refers to the mucous membranes lining the respiratory system as being important to prevent infection, and any less than optimum condition of these membranes would provide another "risk factor" favoring infection by some pathogen.

The first inventor has set forth an hypothesis that his respiratory system and lungs are subject to such "risk factors", and that the first inventor had to invent a new method to prevent invasion by such pathogenic organisms. Consequently, the first inventor has concluded that to minimize the possibility of ending up on oxygen tanks, that it is necessary to prevent the infection of his respiratory system by common pathogens such as pathologic bacteria, viruses, and fungi. It is clear that any one of these pathogens may cause disease. However, the first inventor has the additional hypothesis, that in analogy with many biological systems, it is likely that human diseases can also be caused by a combination of such pathogens that form symbiotic relationships, or associated relationships, similar to well-documented mycorrhizal relationships or the like, which may also change in time. For a description of such mechanisms in biology, for example see Audesirk and Audesirk, 1996 on these and related subjects. Therefore, from the first inventor's point of view, it is possible that any one disease may involve bacteria, viruses, and fungi all at one time, and the mix of these may change vs. time as the disease progresses through various stages.

From the first inventor's point of view, many of his illnesses had begun with either cold-like symptoms or flu-like symptoms. If he got very sick, this often progressed into symptoms mimicking those of pneumonia. So, an initial predominant viral-like infection may evolve into a predominantly bacterial-like infection as time progresses. So, the first inventor views the development of some diseases as progression of various stages, where any one stage may have a peculiar mix of pathogens. The progression of colonies of pathogens vs. time may in fact involve viral, bacterial, and fungal elements called for the purposes herein "symbiotic pathogens" that may make "symbiotic pathogenic colonies". Typically, the composition of those "symbiotic pathogenic colonies" vary with time. As has often been the case in the past, when the first inventor had problems with his respiratory system, standard antibiotics rarely helped. In the first inventor's view, this is because the antibiotics only addressed part of the problem in a typically complex case when "symbiotic pathogens" are causing disease that has at least two components among the three that are viral, bacterial, and fungal components. The view that a given disease is often caused by a time varying mix of bacterial, viral, and fungal pathogens provides the precise reason why the first inventor rarely found commercial antibiotics to be of effective help in overcoming his various lung diseases. Accordingly, the first inventor has theorized that to be able to routinely prevent colds, flus, etc., it is necessary to locate substances that have antiviral and antibacterial and antifungal elements that may be applied to the respiratory system simultaneously.

The first inventor further hypothesized that microscopic portions of his respiratory system at any one time are subject to increased risk of invasion by such pathogens. Any such increased risk site for the purposes herein is defined as a "likely pathogenic invasion site". Once a pathogen "invades" such a "likely pathogenic invasion site", for example within tissue within the lungs, then the pathogens may multiply, causing an infection that may "eat away", or destroy, portions of the lungs of the first inventor. The first inventor has concluded that he needs new methods and apparatus to prevent or block the invasion of pathogens into a likely pathogenic invasion site within his respiratory system. Put another way, the first inventor sought to find a practical method to reduce the risk of infection of the respiratory system by infectious agents.

This is a tall order. The first inventor had theorized about using certain face masks, filtering the air inhaled by the lungs, and passing inhaled air through U.V. light (with the energy of the U.V. below the threshold to produce ozone). Then, the first inventor decided to investigate inhaled chemicals to prevent the invasion by pathogens of a likely pathogenic invasion site. Such chemicals need to be highly volatile, non-toxic, and capable of killing bacteria, viruses, and fungi. The second inventor, Marilyn L. Vail, suggested using *eucalyptus* oil and/or tea tree oil as potential candidates because of her prior research on these substances in her attempts to control internal infections of *Candida albicans*.

The inventors identified a class of chemical compounds that may be used to prevent the invasion of pathogens into the respiratory system. They include *eucalyptus* oil and tea tree oil. Here *eucalyptus* oil includes the essential oil from *Eucalyptus globulus*, and here, tea tree oil is the essential oil from *Melaleuca alternifolia*. The first inventor has found that routinely inhaling these substances has prevented him from getting any colds, flus, or pneumonia in his respiratory system through the date of Apr. 28, 2003—several days before the filing date of this application. The first inventor has been practicing the invention every day commencing on, or before, the first day of September of 1999. As a result of using the invention, the first inventor has had no respiratory infections for over 3½ years as of the filing of Ser. No. 10/429,077. This is despite the fact that the first inventor has had extensive business travels during this time. This is truly remarkable, because the first inventor has often been sick every several months or so before he began practicing the invention.

There is one fine point here of considerable interest. It is stated above that at this point in time, the first inventor has had no respiratory infections for over 3½ years. This is true. Prior to this period when the first inventor caught the flu, it often eventually attacked the lungs in one way or another. When the flu ended up attacking his respiratory system, the first inventor often became very sick and it would often take three weeks or a month for him to recover. When the first inventor returned home from a backpacking trip during December of 1999, the first inventor's wife had a very bad case of the flu. After several weeks, the first inventor actually caught the flu—but it never attacked the respiratory system of the first inventor. In this situation, when the first inventor caught the flu, he became sick very rapidly, had a fever, sometimes a high fever, and he became sore, and typically his joints ached. However, in this particular case, the flu never attacked his respiratory system. In this case, all symptoms disappeared within 48 hours. This was not a life-threatening situation to the first inventor. The first inventor has actually caught similar flus several times during the 3½ years, but in all cases, the flus never attacked his respiratory system while practicing the invention. In retrospect, the first inventor views catching mild cases of the flu to be medically positive, because he is then able to develop suitable antibodies to new strains of influenza without the risk of a catastrophic and life-threatening lung infection. So, when using the phase "the first inventor has not caught the flu since practicing the invention" should rigorously read "the first inventor has not caught the flu in his respiratory system since practicing the invention", which correction applies to any such statements herein, or to any other statements in any other applications by the first inventor on this subject.

Soon after conceiving the invention, the first inventor performed experiments on himself with very crude apparatus. A small bottle of "*eucalyptus* rectified essential oil" made by "aroma-vera" was purchased. It had a blockage near the top of the bottle. Typically, the first inventor shook the bottle with the blockage "down" which caused *eucalyptus* oil to catch in the blockage near the top of the bottle. Then, with the bottle held with the blockage "up", and while holding one nostril closed, the first inventor would inhale very deeply through the other nostril thereby inhaling concentrated vapors of *eucalyptus* oil. Then the process was repeated with the other nostril. The first inventor estimates that the amount inhaled ranged between 0.001 milligrams to 100 milligrams, depending upon the circumstances, and the number of repetitions. The first inventor performed this inhalation immediately before he went "into public", such as into an enclosed public area having one or more human beings within that enclosed area. If there were sick people present that were coughing, or otherwise admitted that they had a cold, the flu, or pneumonia, the first inventor would thereafter similarly inhale concentrated vapors of *eucalyptus* oil every 30 minutes or so. By following this process, as further explained in other preferred embodiments below, the first inventor has not had a cold, the flu, or pneumonia attack his respiratory system for the 3½ years.

The first inventor alternatively used tea tree oil in the above experiments and had similar results. The tea tree oil was in a small bottle marked with the legend "100% PURE AUSTRALIAN TEA TREE OIL" made by Desert Essence.

It is important to note that very strong vapors of either *eucalyptus* oil or tea tree oil were inhaled each time. This happened because of the close proximity of the nose to a pool of highly volatile fluids. However, there were several drawbacks to this method. As a first drawback, on occasion the fluids themselves got sucked up into the nose causing a very unpleasant situation. As a second drawback, if the fluids got on the hands, and then into the eyes, this was also an extraordinarily unpleasant, and perhaps, a dangerous situation. As a third drawback, inhalation through the mouth seemed relatively ineffective from vapors emanating from a simple bottle. As a fourth drawback, inhaling from a pool of highly volatile fluids on airplanes, in elevators, and in crowded places resulted in others being subjected to the strong vapors of essential oils. Having open bottles of flammable fluids on an aircraft is not reasonable today. Accordingly, the inventors have designed an apparatus that provides very strong vapors that may be inhaled, but which also overcomes the above first, second and third drawbacks.

FIG. 1 shows a section view of an apparatus to conveniently generate vapors from *eucalyptus* oil that may be inhaled without suffering the above three drawbacks. *Eucalyptus* oil is chosen for this preferred embodiment, but the use of other suitable essential oils, such as tea tree oil, are discussed below. The apparatus in FIG. 1 is described as a hand-held "atomizer" that is generally designated with element 2. *Eucalyptus* oil 4 is shown in container 6. A piston 8 having O-ring 10 seals against the interior of the container wall. The atomizer has top element 12 that acts as a "button" (hereinafter "top button 12"), and the container has bottom 14. With one hand, placing the middle finger on the button 12 and the thumb on the bottom 14, and squeezing, produces the vaporized droplets of *eucalyptus* oil. One such droplet of *eucalyptus* oil is designated by numeral 16 that is shown in the location to be inhaled by the user.

The vapors of *eucalyptus* oil may be inhaled through the mouth, or through the nose, or through both. Holding one nostril closed at a time allows selective inhalation through one nostril, and then the other, so that the entire respiratory system may be entirely coated with the thin anti-pathogenic film of *eucalyptus* oil.

In FIG. 1, the atomizer is to be operated "substantially vertically" a term that will be defined below. Pressing down on button 12 increases the air pressure in air pocket 18 above the surface of the *eucalyptus* oil 20. This increasing pressure causes *eucalyptus* oil to flow through first entrance 21 of flexible tube 22 and then to first tube 24 that is in turn connected to the atomizer assembly 26. The first entrance 21 of the flexible tube is reinforced and constructed so that it does not collapse under use, and does not make a positive seal against the interior of the container walls that would interfere with functionality. Pressurized air flows thorough second entrance 28 of the second tube 30 that is in turn also connected to the atomizer assembly 26. Using typical designs for atomizers, and the like, the flow of *eucalyptus* oil and pressurized air into the atomizer assembly 26 generates particles of *eucalyptus* oil in the form of a vapor that pass through the exit passage 32 of the atomizer assembly. The atomizer assembly 26 may have any number of suitable valves, one-way valves, spring actuated valves, spring return valves, ball valves, spring loaded ball valves, breather orifices, etc., which are used in the art to make atomizers, and the like, for the purposes herein, however, those elements are not shown in FIG. 1 solely for the purposes of brevity. Any suitable "atomizer means" may be used for atomizer assembly 26.

In FIG. 1, the vaporized *eucalyptus* oil is injected from the exit passage 32 of the atomizer assembly into a cotton ball 34 whose edges are delineated with dashed lines in FIG. 1. Therefore, pushing down on button 12 causes vapors of *eucalyptus* oil to be injected into the cotton ball. Then, the vapors diffuse through the cotton ball for subsequent inhalation.

The tapered mouth orifice 36 is used to inhale vaporized *eucalyptus* oil by mouth. As vaporized *eucalyptus* oil and air is inhaled, any additional air required is provided through nostril orifice 38.

Alternatively, nostril orifice 38 is used to inhale vaporized *eucalyptus* oil by one nostril at a time. One nostril is held shut, and the other one is placed against nostril orifice 38 to inhale through a chosen nostril. One after another, both nostrils may be used to suitably inhale vapors of *eucalyptus* oil.

Other details are shown in FIG. 1. The upper body of the hand-held atomizer 40 is a one-piece unit having tapered mouth orifice 36 and nostril orifice 38. The upper body is attached to the piston 8 using typical fabrication techniques. The spacer 42 is designed to guide the main body 40 during its motion, and it serves as a retainer to prevent the piston 8 from inadvertently coming out of the container 6. The spacer 42 may also have one or more check-valves to function as "breathers" when the unit is initially filled with *eucalyptus* oil, respectively enumerated as 44 and 46, however these elements are not shown in FIG. 1 solely for the purpose of brevity. Spacer 42 has suitably close tolerances, or threads as necessary, to positively engage it to container 6.

FIG. 1 shows the position of piston 8 wherein the top portion of that piston is a distance designated by the legend "X" below the lower portion of the spacer 42. As the top button 12 is pushed downward, the piston 8 is also pushed downward thereby compressing spring 48, and the vaporized droplets of *eucalyptus* oil are formed. The "down stroke" causes the top of the piston to move through a maximum, and extreme value, of X. After completing the "down stroke", and upon removing finger pressure from the button, then compression spring 48 returns the top portion of the piston so as to make contact with the lower portion of the spacer 42, which is the "resting position" of the piston. Typical breather holes, one-way valves, such as ball valves, etc., are used to allow air to flow back into air pocket 18, thus preparing for the next "down stroke". Such a breather hole for the purposes herein is shown as element 50 that is located within a portion of atomizer assembly 26. In the "up stroke", and in this embodiment, air can flow into breather hole 50, and thereafter flow through second tube 30 to air pocket 18 thereby allowing the piston to return to its "resting position". Without such a breather hole, or the like, the piston might permanently stay in the "down stroke" position, or might stay in that position until other air leakages allowed the top of the piston to again contact the bottom portion of spacer 42. To achieve this functionality, various different preferred embodiments contemplate using any number of suitable valves, one-way valves, spring actuated valves, spring return valves, ball valves, spring loaded ball valves, breather orifices, etc., which are used in the art to make atomizers, and the like.

In FIG. 1, refilling the atomizer involves removing the spacer 42, removing the piston 8 from the container 6, and refilling the container. The piston 8 is then inserted into the container 6, and the spacer is reinstalled. Yet one or more ball valves in the piston (not shown) may be used to bleed off extra pressure in the event that is necessary during installation of the piston. Any such pressure relief valves shall have the numerals 52 and 54 respectively, but they are not shown in FIG. 1 solely for the purposes of brevity.

The hand-held atomizer overcomes several of the problems cited earlier. In relation to the above defined "first drawback", by using the cotton ball and the apparatus described, no fluids can get sucked up into a nostril. In relation to the above defined "second drawback", no liquids are generated exterior to the hand-held atomizer, so there is minimal chance of getting *eucalyptus* oil into the eyes. Further, the cotton ball also prevents liquids from being squirted directly into the eyes. In relation to the third drawback, the hand-held atomizer provides proper vaporized *eucalyptus* oil for inhalation by mouth. Therefore, the inventors have designed an apparatus and provided methods of operation that provide very strong vapors that may be inhaled, but which also overcome the previously defined first, second and third drawbacks.

There are many variations on the above preferred embodiment. The container 6 may be fabricated from any suitable material, including any type of plastic, or any type of transparent or translucent plastic of any coloration. Transparent or translucent plastics are convenient so that the presence or absence of the *eucalyptus* oil, and the surface of the *eucalyptus* oil 20, may be easily determined by visual inspection. The upper body of the hand-held atomizer 40 having tapered mouth orifice 36 and nostril orifice 38 may be made of any suitable material, including any type of plastic, or any type of transparent or translucent plastic of any coloration. Transparent or translucent plastics are convenient to determine the condition and extent of the cotton ball 34.

For proper operation, the cotton ball 34 should substantially fill and make contact with the interior walls of the upper body of the hand-held atomizer 40. The cotton ball 34 is convenient, but any material may be used as a substitute that has "cotton-ball like qualities" for the purposes of the invention herein that otherwise also avoids the above defined first, second, and third drawbacks. No toxic materials may be used to replace the cotton-ball. Spacer 42 may be fabricated from any material and may be disposed in its location in FIG. 1 using any suitable attachment methods including friction fitting, matching threads, retainer notches, and the like. Any suitable "retainer means" may replace spacer 42.

The dimensions of the nostril orifice 38 are chosen so that it conveniently extends beyond the radial extent of the container 6 and into the nostril for use when held in place by the fingers. The exterior of the container 6 has a first radius R1 (not shown in FIG. 1) that is typically ½ inches, and a first vertical length, or extent, L1 (not shown in FIG. 1) that is typically 1¾ inches tall. Here, the radius is defined as the radial distance away from the vertical axis of the container 6. For the record, FIG. 1 is not to scale. The nostril orifice 38 has a second radial extent R2 (not shown in FIG. 1) that is typically 1¼ inches and a nostril orifice diameter NOD (not shown in FIG. 1) that typically ranges between 3/16 inches O.D. to ¼ inches O.D. for convenient insertion into the nose, but many other dimensions are possible. The diameter NOD is chosen so that the nostril orifice can go into the interior of a typical nostril.

The tapered mouth orifice 36 has a third radial extent R3 (not shown in FIG. 1) that is typically 1½ inches, and an mouth inhalation diameter MID (not shown in FIG. 1) that is typically 1½ inches OD. The tapered mouth orifice may not be circular, and may be any suitably chosen shape to conveniently fit into the mouth. The overall maximum vertical dimension of the hand-held "atomizer", which is the distance between the button 12 and the bottom 14, is typically 3 inches.

In the above, it was stated that the atomizer is to be operated "substantially vertically". The atomizer is to be held in a "substantially vertical orientation" for proper operation. The definition of these terms are as follows. For proper operation, the first entrance 21 of the flexible tube must be immersed in the fluid 4, and must be located below the fluid level 20 so that fluid may be properly atomized ("first condition"). In the above embodiment, the second entrance 28 of the second tube is used to provide air under pressure to the atomizer assembly 26, so that the second entrance 28 must also be located above the fluid level 20 so for proper atomization of the fluid ("second condition"). Lastly, various means, including breather holes and suitable valves, have been described which allow the piston to return from the "down stroke" to its "resting position", and consequently, the orientation of the atomizer in FIG. 1 should be sufficiently vertical so as not to interfere with such means ("third condition"). Any hand-held "atomizer" that is generally designated with element 2 in FIG. 1 that is an orientation such that the first, second, and third conditions are satisfied in this paragraph is in a position that is "substantially vertical". Accordingly, the atomizer is operated "substantially vertically" which is in a "substantially vertical orientation". In general, when the atomizer is held in the hand, its longitudinal axis along its length is at an angle θ with respect to true vertical (which angle is not shown in FIG. 1 for brevity). This longitudinal axis is parallel to the vertical sides of the container 6. The maximum "tilt angle" at which the atomizer fails to meet the first, second, and third conditions depends upon the particular distance from the interior of the bottom of the container to the top of the fluid level 20, when the atomizer is held in the true vertical position, and that particular distance is identified by the legend Y in FIG. 1. Accordingly, there is reason to maintain a reasonable distance between the top of the fluid and the bottom of the piston, and that reasonable distanced is defined by the legend Z in FIG. 1. When X achieves its maximum value in the "down stroke" (XMAX) then Z maintains its minimum value at that position (ZMIN) for any given level of fluid in the container Y for $\theta=0$ degrees. The variables XMAX, ZMIN and θ are not shown in FIG. 1 for the purposes of simplicity. The above comments may be suitably reformulated in terms of the volume of the fluid 4 inside the container 6. For future reference, the inside diameter of the container 6 is the parameter IDC, that is not shown in FIG. 1 for the purposes of brevity.

In earlier disclosure, element 16 was identified as a droplet of *eucalyptus* oil. There are two additional comments here. First, as is typical with most atomizer devices, there is a statistical distribution of droplet sizes and volumes produced depending upon a number of factors including the fluid, its viscosity, the design of the atomizer system, and the force applied to the button 12. The inventors include herein by reference all art in the field related to the production and measurements of such statistical distributions of droplet sizes. Second, any droplet 16 in FIG. 1 may also stand for any other droplet of any other fluid described to this point or hereafter in this application.

There are other variations of the apparatus. The functional elements in FIG. 1 may be reconfigured to fit onto a screw-on cap that in turn screws onto a bottle having *eucalyptus* oil. The bottle may in fact be the original bottle of *eucalyptus* oil that arrived from a manufacturer, so that the refilling process becomes easier. However, this is a minor variation of the invention, and in the interests of brevity, shall not be described in detail.

Tea tree oil may be substituted in the above for *eucalyptus* oil. Put another way, element 4 in FIG. 1 may be chosen to be tea tree oil instead. The use of tea tree oil in the apparatus is similar, except that it is possible that the atomizer assembly 26 may be changed because of the different properties that tea tree oil may have, including different viscosity, density, vapor pressure, etc. Each atomizer assembly may be specifically designed for the oil to be atomized. Each atomizer, or "atomizer means", may in fact be specific to different suppliers of tea tree oil or *eucalyptus* oil in that different suppliers may produce oils having different characteristics as they affect vaporization by the atomizer.

Yet further, element 4 may be chosen to be pure *eucalyptus* oil; pure tea tree oil; any mixture of *eucalyptus* oil and tea tree oil; any mixture of one or more components from *eucalyptus* oil and one or more components from tea tree oil (which components are defined below); any mixture of *eucalyptus* oil and distilled water; any mixture of tea tree oil and distilled water; and any mixture of *eucalyptus* oil, tea tree oil, and distilled water; and any mixture of the following—(a) one or more components from *eucalyptus* oil and (b) one or more components from tea tree oil and (c) any percentage of distilled water. Therefore, element 4 may be chosen to be any of the above defined fluids in FIG. 1. Element 4 may be chosen to be any essential oil, or any mixture of essential oils, from those listed in the below defined "List of Essential Oils".

In FIG. 1, the cotton ball 34 may be replaced with other substances. For example, the cotton in preferred embodiments can be replaced with plastic material having uniform sized holes. In such a case, the size of the droplet 16 in FIG. 1 may be adjusted in size. Alternatively, the cotton may be removed entirely provided the atomizer assembly 26 in FIG. 1 produces relatively small droplet sizes. Alternatively baffles with holes may be placed across the interior of orifices 36 and 38 to control droplet size. Yet alternatively, if the cotton is removed, the vapor droplets from orifice 38 may be injected into an expansion chamber, where the droplets diffuse, which are in turn inhaled through yet another orifice attached to that injection chamber (not shown in FIG. 1). These are all examples of means to control the droplet size from the hand-held atomizer apparatus. Such means can be used to provide a concentrated stream of essential oil vapors from the hand-held inhaler apparatus. Such means can be used to provide a fine spray of droplets. The size of the droplets can range from the size of molecules to droplets up to 0.050 inches OD.

The device shown in FIG. 1 may also be used to generate an aerosol. According to the Webster's New World™ Dictionary of American English, Third College Edition, edited by Victoria Neufeldt and David Guralnik, Simon & Schuster, Inc., New York, N.Y., 1988 ("Neufeldt and Guralnik, 1988), an entire copy of which is incorporated herein by reference, an "aerosol" is "a suspension of colloidal particles in a gas". If small particles of solid materials are made into a colloidal suspension within the fluid 4 present in FIG. 1, then the hand-held atomizer apparatus in FIG. 1 would produce an aerosol. The small solid materials would be surrounded by fluid as the solid materials would emerge from hand-held atomizer apparatus in the form of droplets. The solid materials dispersed within the fluid within the hand-held atomizer apparatus could be antibacterial drugs, antiviral drugs, or antifungal drugs to be used for specific treatment of diseases in the human respiratory system.

FIGS. 2-6 show another preferred embodiment of the invention.

Figure 2:
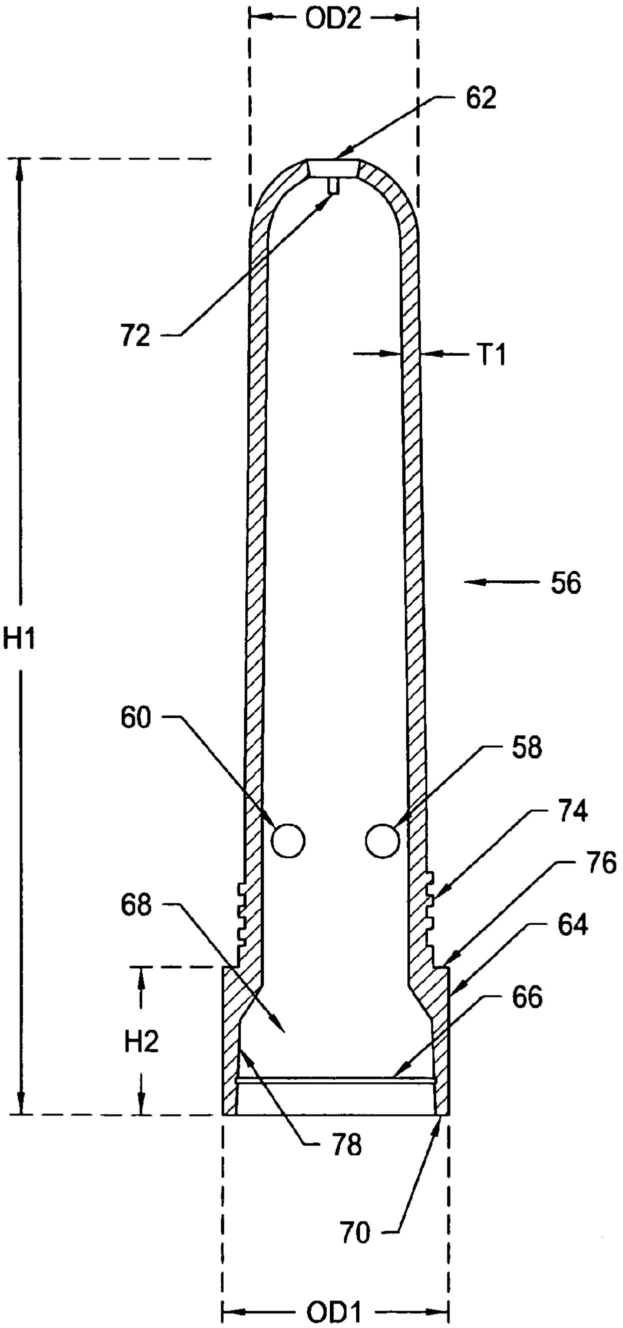
FIG. 2 shows a cross section view of an Inhaler Body.

FIG. 2 shows a cross section view of the Inhaler Body generally designated as element 56. Air inlet holes 58 and 60 allow air to enter the Inhaler Body when it is assembled (see FIG. 5). Vapor outlet orifice 62 allows vapor from the interior of the Inhaler Body to be inhaled into the nose or into the mouth. The Inhaler Body is comprised of a plastic made in an injection mold. The plastic is resistant to essential oils that has a wall thickness shown by the legend T1 in FIG. 2. In one preferred embodiment, the wall thickness T is approximately 0.050 inches. The overall height of the Inhaler Body is shown by the legend H1. In one preferred embodiment, the height H1 is approximately 2.73 inches. The Inhaler Body has hand-held grip 64. In one preferred embodiment, the hand-held grip has fine groves to aid in holding the device, but those fine groves are not shown in FIG. 2 for the purposes of simplicity. The hand-held grip 64 on the Inhaler Body is held by the fingers when inserting the vapor outlet orifice 62 into the nose (or mouth). The outside diameter of the Inhaler Body in the vicinity of the hand-held grip is shown as legend OD1. In one preferred embodiment, OD1 is approximately 0.635 inches. The height of the hand-held grip is shown by the legend H2. In one preferred embodiment, H2 is approximately 0.423 inches. The outside diameter of the upper portion of the Inhaler Body is shown as the legend OD2 in FIG. 2. In one preferred embodiment, OD2 is approximately 0.490 inches as shown in FIG. 2. The upper portion of the Inhaler Body is tapered through a small angle θ so that it can be removed from the injection mold, although that angle is not shown in FIG. 2 for simplicity. Inhaler Plug recession 66 is used to latch the Inhaler Plug into place as further explained in relation to FIG. 3. The Inhaler Plug (shown in FIG. 3) fits within region 68 within the Inhaler Body. The Inhaler Body has lower end 70. The Inhaler Body has internal cross bar 72 for purposes to be described later, and possesses threads 74. The Inhaler Body also has positive sealing surface 76 so that the Inhaler Cap seats in place (see FIG. 6). The Inhaler Body also has positive sealing surface 78 that allows the mating surface of the Inhaler Plug to seat in place (see FIG. 5).

Figure 3:
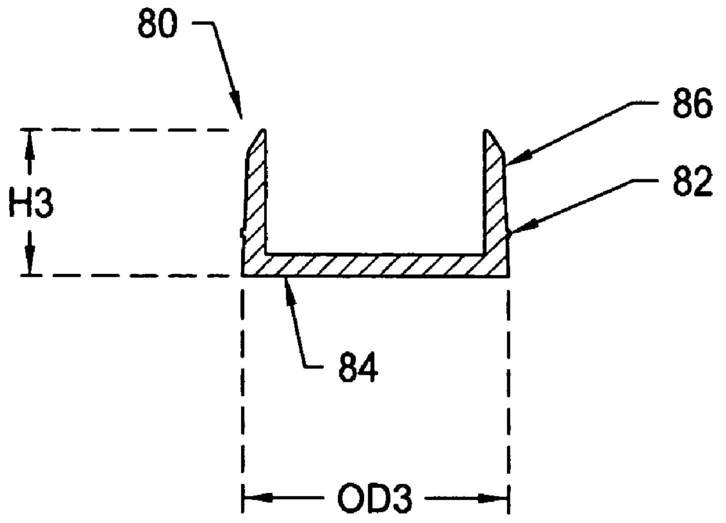
FIG. 3 shows a cross section view of an Inhaler Plug.

FIG. 3 shows a cross section view of Inhaler Plug 80 that possesses extruded ridge 82. The Inhaler Plug 80 is made of plastic in a plastic injection mold that is resistant to essential oils. The Inhaler Plug 80 is forced into the lower end of the Inhaler Body, and fits within region 68 of the Inhaler Body shown in FIG. 2. When pressed into place, the bottom surface 84 of the Inhaler Plug does not protrude below lower end 70 of the Inhaler Body. When pressed into place, the extruded ridge 82 positively "snaps" into place within the Inhaler Plug recession 66 so that it will not fall out of the Inhaler Body. In one preferred embodiment, it takes a minimum force of 20 lbs and a maximum force of 25 lbs to force the Inhaler Plug into place within region 68 of the Inhaler Body. The Inhaler Plug has the height shown by the legend H3 in FIG. 3. In one preferred embodiment, H2 is 0.264 inches. The outside diameter of the Inhaler Plug at the location of its bottom surface 84 is shown by the legend OD3 in FIG. 3. In one preferred embodiment, OD3 is 0.559 inches OD. The dimensions H2 and OD3 are such that the entire Inhaler Plug fits within region 68 of the Inhaler Body in FIG. 2 and does not protrude below the lower end 70 of the Inhaler Body. The Inhaler Plug has positive sealing surface 86 that is used to seat against sealing surface 78 within the Inhaler Body. See FIGS. 5 and 6 for assembly of the Inhaler Plug within the Inhaler Body.

Figure 4:
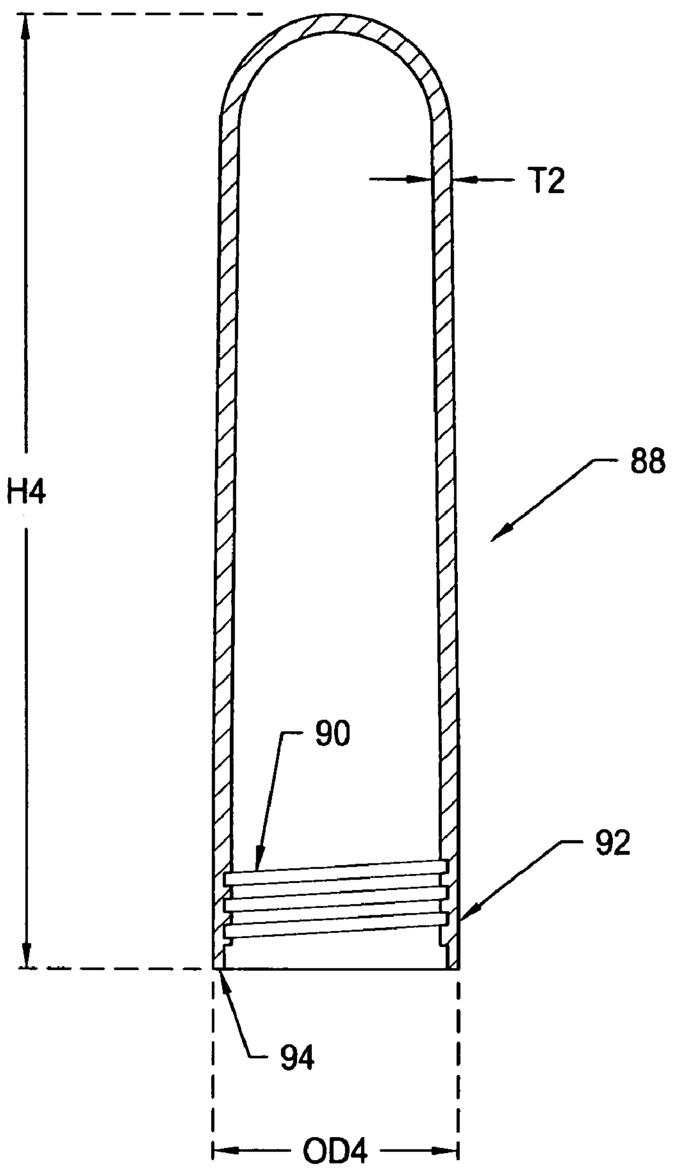
FIG. 4 shows a cross section view of an Inhaler Cap.

FIG. 4 shows a cross section view of the Inhaler Cap 88. The Inhaler Cap is made from plastic in a plastic injection mold that is resistant to essential oils. The Inhaler Cap possesses interior threads 90 that screw onto threads 74 of the Inhaler Body. The wall thickness of the Inhaler Cap is shown by the legend T2 in FIG. 2. In a preferred embodiment, T2 is 0.050 inches. The vertical height of the Inhaler Cap is shown by the legend H4 in FIG. 4. In one preferred embodiment, H4 is 2.43 inches. The Inhaler Cap has lower end 92. At the lower end of the Inhaler Cap, the outside diameter of the Inhaler Cap is shown by the legend OD4 in FIG. 4. In one preferred embodiment, OD4 is 0.642 inches OD. The Inhaler Cap has lower sealing surface 94 that seals against positive sealing surface 76 of the Inhaler Body. A positive seal is necessary to retain the highly volatile essential oils as explained in relation to FIG. 6.

Figure 5:
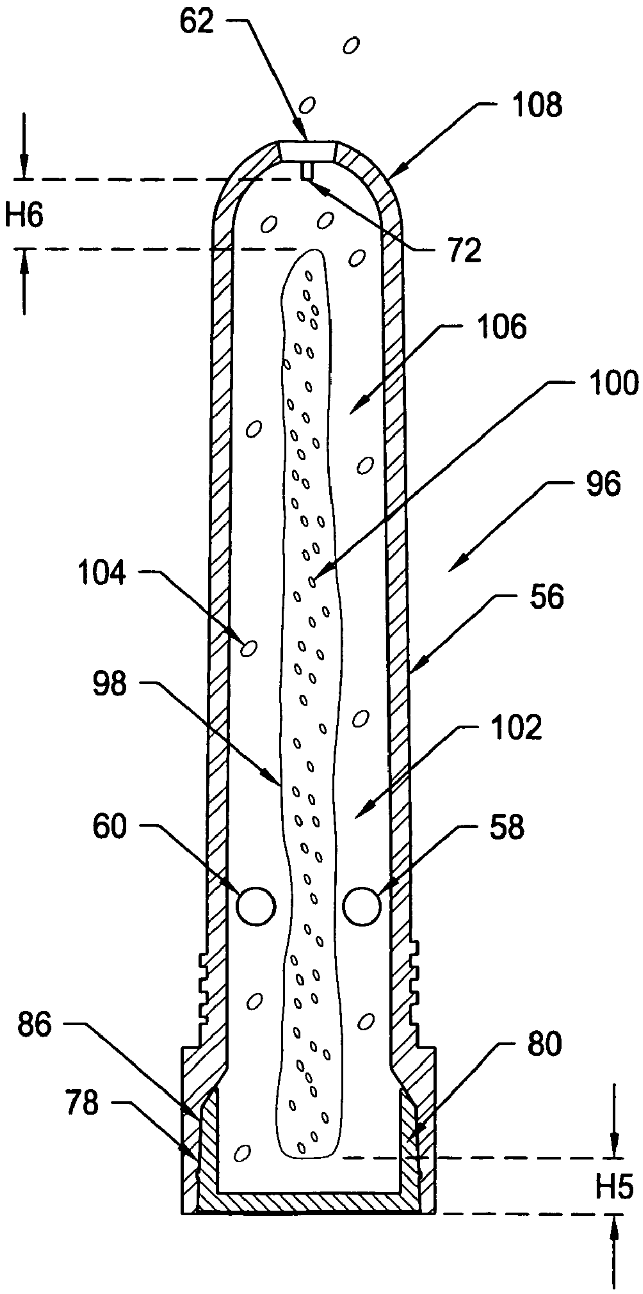
FIG. 5 shows a cross section view of an assembled Inhaler ready to be inserted into the nose.

The cross section of an assembled Inhaler ready to be inserted into the nose or mouth is generally shown as element 96 in FIG. 5. In one preferred embodiment, a pure cotton insert 98 has been soaked in an essential oil shown by element 100. The pure cotton insert is preferably of the type of cotton that is sterile and is free from any chlorine or other chemicals that are sometimes used to bleach cotton white. Examples of the essential oil includes *Eucalyptus* Oil, Tea Tree Oil, a mix of these oils, or any other essential oil, or mix of those oils, shown in the List of Essential Oils. After the pure cotton insert 98 has been soaked in an essential oil, then it is inserted within the interior of the Inhaler in position 102 that is shown in FIG. 5. Thereafter, the Inhaler Plug 80 is assembled into the Inhaler Body 56. When assembled, the Inhaler Plug has sealing surface 86 that is used to positively seat against sealing surface 78 within the Inhaler Body. These mating surfaces 78 and 86 produce a vapor-tight seal. The vapor-tight seal is necessary to prevent the vapors from the essential oils from escaping through the bottom of the Inhaler. The essential oil 100 has relatively high vapor pressures and evaporate forming an essential oil vapor 104 within the interior chamber 106 of the assembled Inhaler 96.

When inhaling vapors from the Inhaler shown in FIG. 5, the tip of the assembled Inhaler 108 is generally placed near to, or inside, a nostril of the nose. Typically holding the other nostril closed with a finger, the essential oil vapor 104 is inhaled through vapor outlet orifice 62 into the nose, and thereafter into the sinuses, the lungs, and other portions of the human respiratory system. When inhaling from the Inhaler, fresh air is sucked into air inlet holes 58 and 60 which allows the essential oil vapor 104 to travel towards the vapor outlet orifice 62 and into the nose.

The hand-held apparatus in FIG. 5 is a novel device that is used to inhale essential oil vapors. Many devices have been heretofore used to produce vapors from essential oils including placing the oils into boiling water; using aroma lamps (both candle and electric powered); using so-called passive "diffusers" that are often hung around the neck, or hung in cars, which contain essential oils dissolved in other media such as rock salt, clays, sands, fibrous materials, etc.; using aromatherapy discs; using steam vaporizers where essential oils are put into the water of the vaporizer (both "cold" mechanical types and electric heater types); using humidifiers having essential oils; using the direct inhalation of essential oil vapors from bottles; using the inhalation of vapors from essential oils placed on tissue papers; and the inhalation of essential oils into the nose that are rubbed on the hands. When humans inhale vapors from such sources, the dose of the inhaled vapor is extremely variable. However, the Inhaler shown in FIG. 5 provides a much more controlled dose of essential oil vapors. Further, the lung capacity of humans are on the average monotonically related to the size and weight of the individual. Therefore, if a small size person inhales deeply, he or she will obtain a lesser dose of the vapor from the essential oils than will a larger person. Therefore, this embodiment of the Inhaler has the virtue that is provides a dose that is related to the weight of the individual, other factors being held constant. Further, with the preferred embodiment shown in FIG. 5, for any one individual, he or she can determine how to replicate the effective amount of vapor to inhale. Such replication is not possible with other means of inhaling essential oil vapors. Accordingly, a virtue of the Inhaler shown in FIG. 5 is that any one individual may consistently, from one day to the next, obtain a controlled amount of vapor from the essential oils. In the field of aromatherapy, the lack of devices to administer relatively controlled doses has been a significant problem. Therefore, the preferred embodiment of the Inhaler shown in FIG. 5 is able to provide relatively controlled doses of vapors from essential oils, and this is a major innovation and a major improvement in the field of aromatherapy.

After extended usage, the amount of vapor within the Inhaler decreases. Accordingly, using techniques described below in relation to FIG. 6, the position of the cotton insert may be adjusted towards the tip of the assembled Inhaler 108 or towards the Plug 80 in the Inhaler. Legends H5 and H6 define the relevant distances in FIG. 5. If H5 is 0 inches, then the vapor inhaled through vapor outlet orifice 62 is minimized. If H6 is 0 inches, then the vapor inhaled through vapor outlet orifice 62 is maximized.

In FIG. 5, it is also worth point out that the internal cross bar 72 has an important purpose. If H6 is 0, then the upper portion of the cotton insert 98 rests against the cross bar 72. In this position, if a baby inadvertently sucks on the vapor outlet orifice 62, then the baby cannot suck out the cotton insert 98. This is important because although essential oil vapors might not harm a child, if a child instead were to inadvertently ingest the essential oil 100 within the cotton insert 98, then it could cause potential poisoning of the infant. If the cross bar 72 were not in the position shown, then it might be possible for a baby to suck the cotton insert out through the vapor outlet orifice 62.

As the temperature of the cotton insert 98 having essential oil 100 increases, then the vapor pressure of the volatile essential oils increase, and stronger vapors may be inhaled through the vapor outlet orifice. Individuals may learn to obtain consistent doses at room temperature. Then again, if the individual carries the Inhaler in his or her pocket, he or she may learn to adjust the dosage for the higher temperature.

Figure 6:
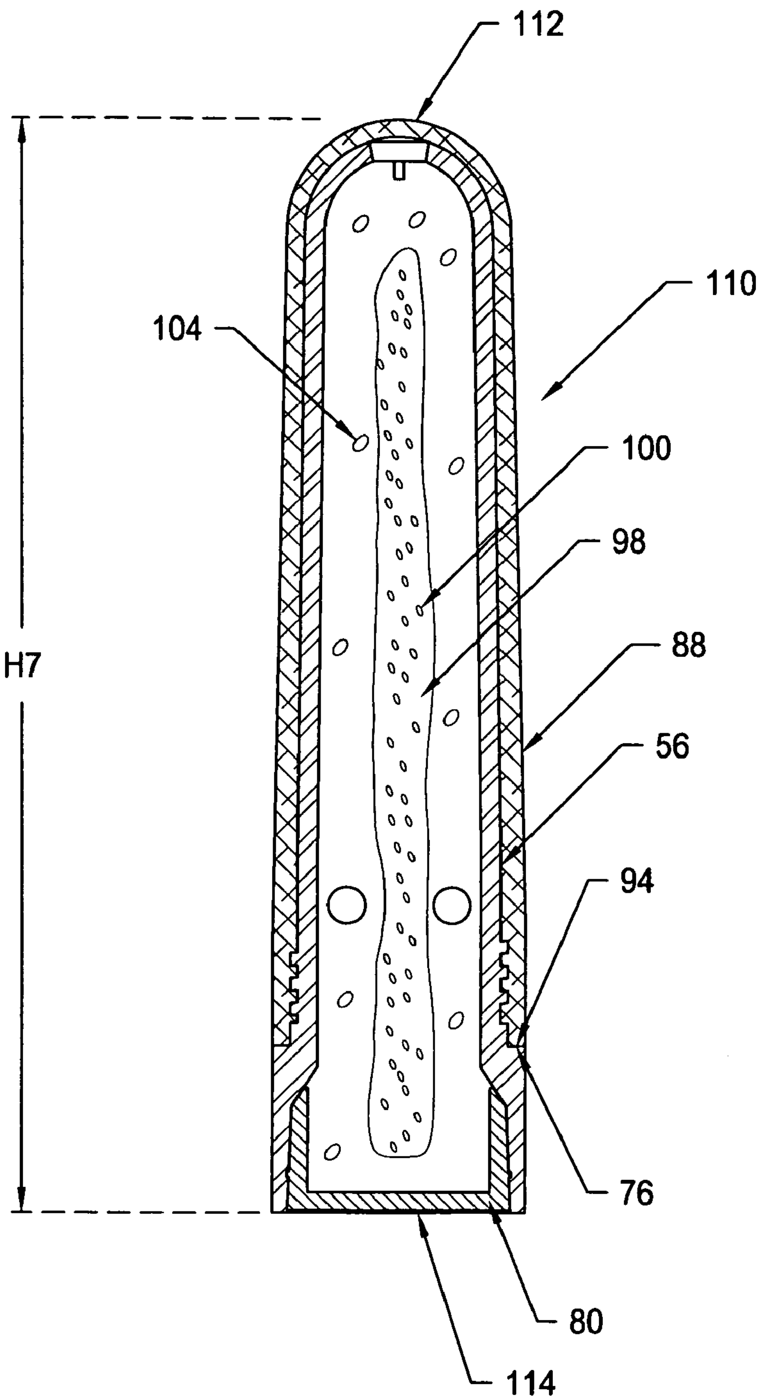
FIG. 6 shows a cross section view of an Inhaler with its cap assembled in place.

FIG. 6 shows the cross section of an Inhaler with its cap assembled in place that is generally designated by element 110. If the Inhaler in FIG. 5 is left out in the air, the vapors will eventually evaporate out of the Inhaler through its vapor outlet orifice 62. So, for storage of the Inhaler, the Inhaler Cap must be installed. FIG. 6 shows the Inhaler Body 56, the Inhaler Plug 80, the Inhaler Cap 88, the cotton insert 98 that has been soaked in an essential oil 100, and the essential oil vapor 104. The overall height of the Inhaler with its cap installed is defined to be the legend H7. In the preferred embodiment herein H7 is approximately 2.85 inches. It is now evident why the positive sealing surface 76 of the Inhaler Body must make a good seal against the lower sealing surface 94 of the Inhaler Cap when the Cap is "torqued down" by finger tightening. If this seal fails, then the highly volatile essential oil vapors can leak out of the Inhaler with the Inhaler Cap installed.

In FIG. 6, the top portion of the Inhaler Cap is identified with element 112. If this top portion is "tapped" onto the surface of a table, then H6 identified in FIG. 5 will go to 0 inches, and after removal of the Inhaler Cap, the inhaled vapor will be more concentrated. In FIG. 6, the bottom portion 114 of the Inhaler is identified with element 114. If this bottom portion is "tapped" onto the surface of a table, then H5 will go to 0 inches, and after removal of the Inhaler Cap, the inhaled vapor will be less concentrated.

In FIGS. 5-6, the pure cotton insert 98 may be replaced by any suitable material. The essential oil 100 is held within the cotton insert under its own surface tension. So, any porous material of any type that is sterile, and which will hold the essential oil under its own surface tension can be used to substitute for pure cotton insert 98 in FIGS. 5-6. There are many possibilities. Many different fibrous mediums which are sterile may be used. For example, hollow fibrous tubes may be used. In yet another embodiment, a small atomizer assembly may be suitably attached to the an insert that replaces insert 98 in FIGS. 5-6. These improvements provide means to control the droplet size of the essential oil vapor (that shown as element 104 in FIG. 5) that is produced from the hand-held inhaler apparatus. Such means may be used to provide a more potent, or concentrated, steam of essential oil vapors from the hand-held inhaler apparatus.

Figure 7:
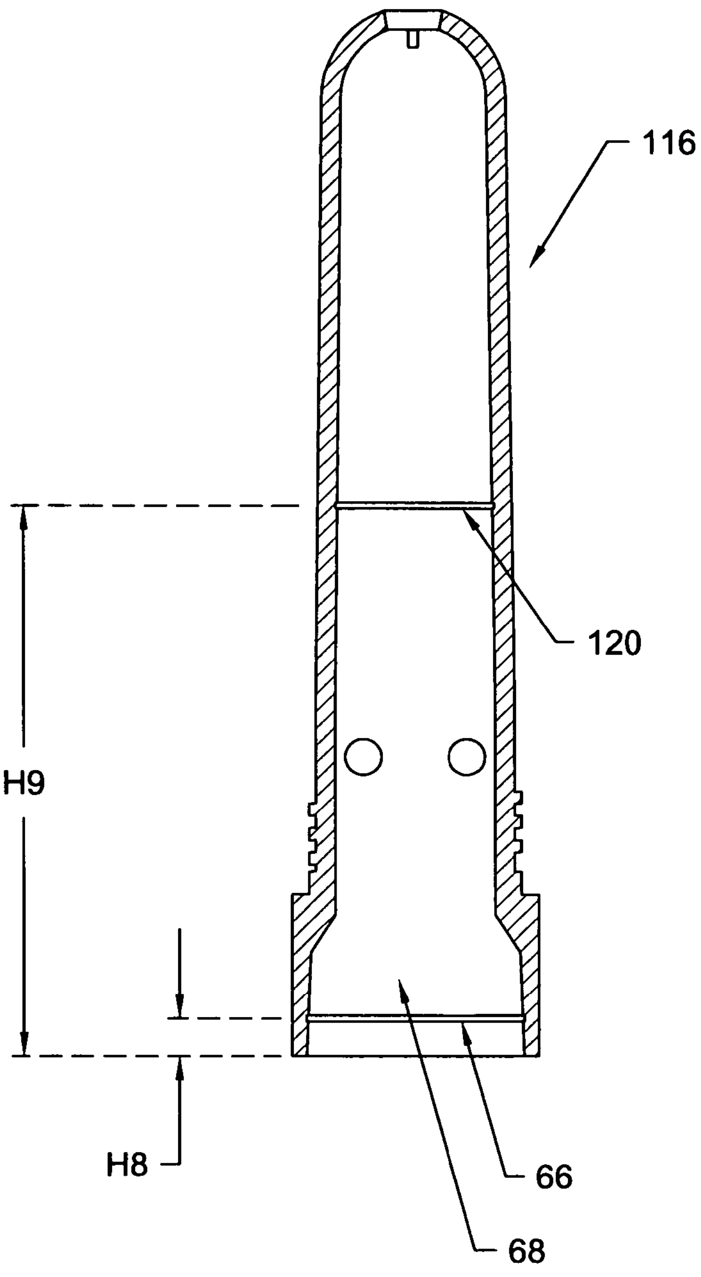
FIG. 7 shows another cross section view of an Inhaler Body with provision for the installation of a Separator.

FIG. 7 shows the cross section of another preferred embodiment of an Inhaler Body generally designated by element 116. This Inhaler Body 116 is identical to the Inhaler Body 56 in FIG. 2 except Inhaler Body 116 has an additional recession in the interior wall of the Inhaler Body called the Separator recession. FIG. 7 shows the Inhaler Plug recession 66 at the position designated by legend H8 that is identical to that of Inhaler Body 56 shown in FIG. 2. FIG. 7 shows the Separator recession 120 at the vertical position designated by legend H9. This Separator recession 120 is the new additional recession. The Inhaler Plug 80 of FIG. 3 fits within region 68 of Inhaler Body 116.

Figure 8:
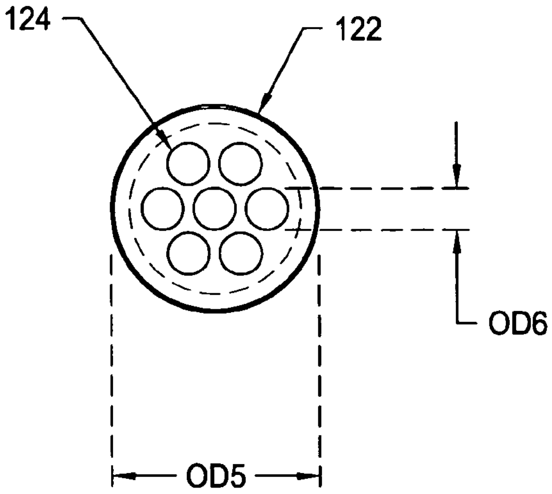
FIG. 8 shows the top view of a Separator.

FIG. 8 shows the top view of Separator 122. It has an approximate outside diameter shown by the legend of OD5 in FIG. 8. In the preferred embodiment shown in FIG. 8, the Separator has a total of 7 breather holes. One such breather hole is labeled with element 124. Each such breather hole has an outside diameter of OD6.

Figure 9:
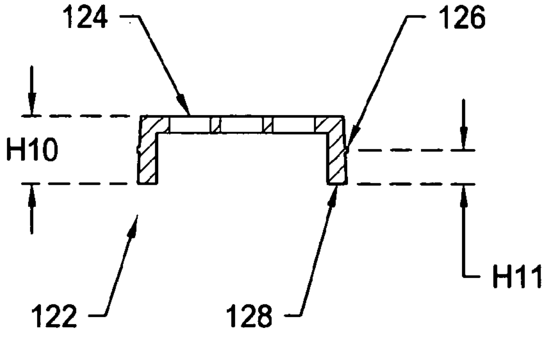
FIG. 9 shows a cross section view of a Separator.

FIG. 9 shows the cross section view of Separator 122. A side view of breather hole 124 is also shown in FIG. 9. The height of the Separator is shown by the legend H10 in FIG. 9. The Separator possesses extruded ridge 126. The extruded ridge 126 is a distance defined by the legend H11 above the lower edge 128 of the Separator.

Figure 10:
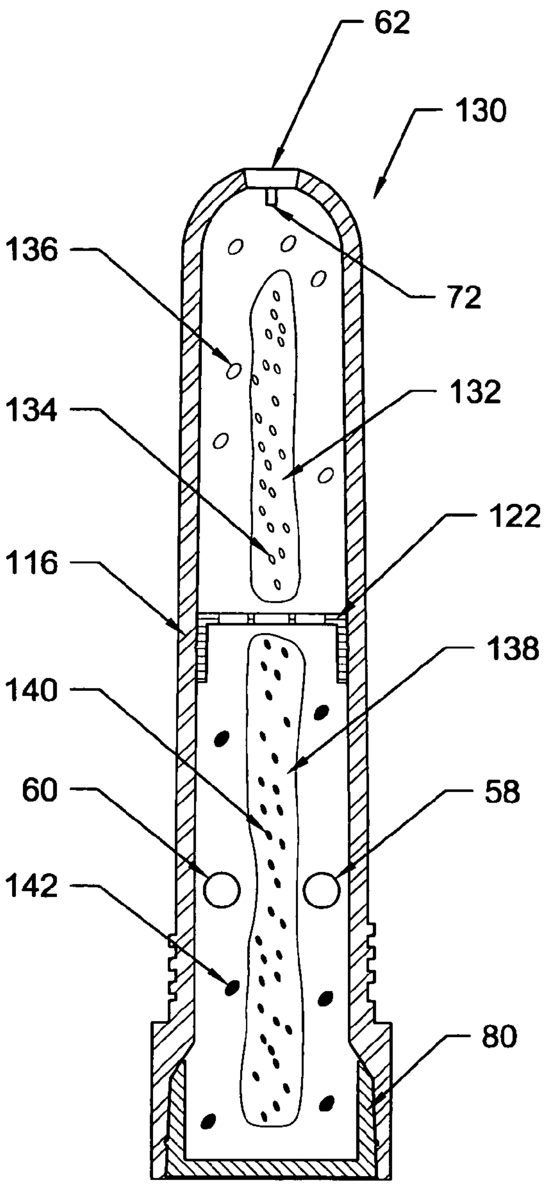
FIG. 10 shows a cross section view of an assembled Inhaler with an installed Separator.

FIG. 10 shows the cross section view of an assembled Inhaler with Separator installed that is generally shown as element 130. The Inhaler shown in FIG. 10 is assembled as follows. Upper cotton insert 132 is soaked in first essential oil 134 which is then installed within Inhaler Body 116 that produces first essential oil vapor 136. Then the Separator 122 is installed within Inhaler Body 116. During this installation, the extruded ridge 126 of the Separator (in FIG. 9) is snapped into place into the Separator recession 120 (in FIG. 7) within the Inhaler Body 116. Then lower cotton insert 138 is soaked in second essential oil 140 that is then installed within the Inhaler Body 116 that produces second essential oil vapor 142. Then Inhaler Plug 80 is installed within Inhaler Body 116.

For use, the vapor outlet orifice 62 is typically inserted into one nostril, with the other nostril held closed with a finger. As an individual inhales, a mixture of vapors from first essential oil vapor 136 and second essential oil vapor 142 are inhaled into the lungs. Air flows into the Inhaler Body 116 through air inlet holes 58 and 60 and through the breather holes in the Separator. This design is particularly useful if first essential oil 134 is chemically or physically reactive with second essential oil 140. The separated chambers allow the combination of vapors to be inhaled from essential oils that may be otherwise chemically or physically reactive. First essential oil 134 may be any pure essential oil or any mixture of those essential oils found in the List of Essential Oils. Second essential oil 140 may be any pure essential oil or any mixture of those essential oils found in the List of Essential Oils.

Figure 11:
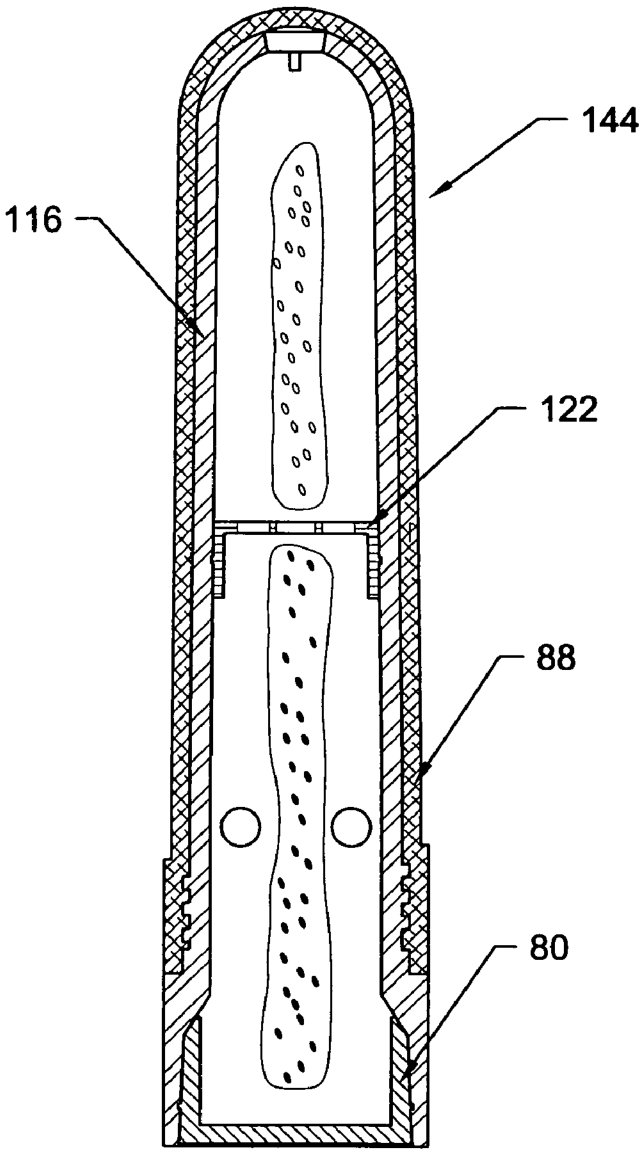
FIG. 11 shows a cross section view of an assembled Inhaler with a Separator installed and with the Inhaler Cap installed.

FIG. 11 shows the cross section view of the Inhaler in FIG. 10 with Inhaler Cap 88 properly installed for long term storage that is generally designated with element 144. The other elements shown in FIG. 11 have been previously defined in relation to FIG. 10.

From the above description, it is evident that two or more Separators may be used in Inhalers. Therefore, Inhalers may be fabricated having three or more separate cotton inserts in different portions of the Inhaler. Each such cotton insert can be soaked in a different essential oil, or combination of essential oils. Therefore, Inhalers have been described that have two or more cotton inserts within different chambers separated by two or more Separators. Further, different separators can be designed that are "Longitudinal Separators", which separate cotton inserts longitudinally. In such a case, different portions of the Inhaler are divided into different azimuthal sections. However, these are minor variations of the preferred embodiment of the invention.

The apparatus described in FIG. 1, and FIGS. 2-11, are all embodiments of hand-held inhalers, hand-held inhaler apparatus, hand-held inhaler devices, hand-held atomizer apparatus, and hand-held inhaler means. So, the apparatus in FIG. 5 can be called a hand-held inhaler, a hand-held inhaler apparatus, a hand-held inhaler device, a hand-held atomizer apparatus, or a hand-held inhaler means. Examples of "at least one orifice attached to a hand-held atomizer apparatus" are either element 36, or element 38, in FIG. 1. Another example of "at least one orifice attached to a hand-held atomizer apparatus" is the vapor outlet orifice 62 in FIG. 2. Similarly, these elements 36, 38, and 62 may also be described as "at least one orifice attached to a hand-held inhaler".

In several preferred embodiments, *eucalyptus* oil is the essential oil from *Eucalyptus globulus*. In other embodiments, *eucalyptus* oil may mean any oil in the *eucalyptus* family including *Eucalyptus globulus, Eucalyptus smithii*, etc.

Test Chamber

Heretofore, standard techniques have been used to measure the antipathogenic properties of essential oils. These methods generally employ the physical contact of the test essential oil with the test pathogen. Typically, a culture of bacteria is grown in a medium in a petri dish, and then filter paper soaked in an essential oil is placed on top of the culture. If the essential oil is effective, then the bacteria are killed out to a certain radius away from the filter paper soaked in the essential oil. For further references on such techniques, please refer to the chapter entitled "The Aromatogram" on pages 33-36 of Schnaubelt, 1998, an entire copy of which is incorporated herein by reference. Typical results from those tests appear in the table entitled "Effectiveness of Essential Oils Against Microorganisms" on page 35 of Schnaubelt, 1998, an entire copy of which is incorporated herein by reference.

Many different references are cited on the subject of testing the antipathogenic properties of essential oils in the book entitled "Aromatherapy for Health Professionals, by Shirley Price and Len Price, Second Edition, Churchill Livingstone, New York, N.Y., 1999 ("Price and Price, 1999"), an entire copy of which is incorporated herein by reference. In particular, please see pages 66-68 of Price and Price, 1999. Table 4.4 on pages 70-71 of Price and Price, 1999, shows typical results for the antibacterial properties of selected essential oils, an entire copy of which is incorporated herein by reference. Table 4.5 on page 73 of Price and Price, 1999, shows typical results for the antifungal effects of selected essential oils, an entire copy of which is incorporated herein by reference. Table 4.6 on page 75 of Price and Price, 1999, shows typical results for the antiviral properties of selected essential oils, an entire copy of which is incorporated herein by reference.

Additional references on the antipathogenic properties of essential oils are provided on pages 91-102 of Schnaubelt, 1999, an entire copy of which is incorporated herein by reference.

As previously stated, the above cited reference generally describe the physical contact of the test essential oil with pathogens under test. However, a new test is required that tests the antipathogenic properties of the vapors from essential oils on selected pathogens. That is the purpose of the apparatus shown in FIG. 12.

Figure 12:
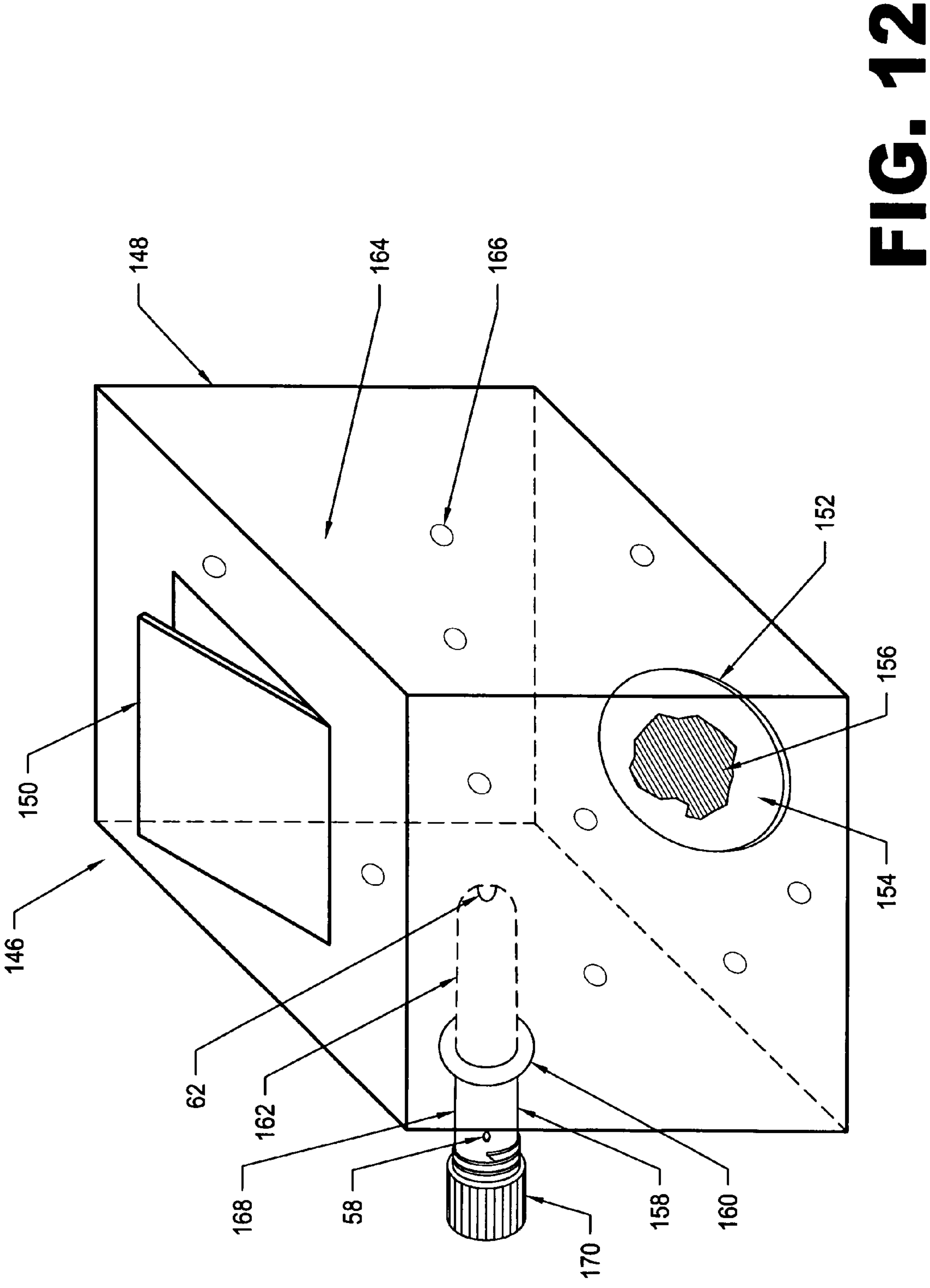
FIG. 12 shows a perspective view of the Inhaler Test Chamber to test the sensitivity of pathogens to vapors produced within an Inhaler.

FIG. 12 shows a perspective view of the Inhaler Test Chamber 146. A sealed test chamber 148 has an access door 150. FIG. 12 shows this access door in the open position. However, during tests of pathogens, this access door is in the closed position. A petri dish 152 contains a suitable pathogen growing medium 154 on which is grown a test pathogen 156 such as anthrax (*Bacillus anthracis*), for example. A Test Inhaler 158 is inserted through grommet 160 so that the upper portion of the Inhaler 162 protrudes through and into the interior of the Inhaler Test Chamber 164. The vapor outlet orifice 62 allows vapor 166 to accumulate within the Test Chamber. The essential oils evaporate producing the vapor. Here, essential oils in the vapor phase are tested in the Inhaler Test Chamber. The air inlet hole 58 explicitly shown in FIG. 12, and air inlet hole 60, must be blocked off on the exterior of the Inhaler Test Chamber. These air inlet holes can be blocked with simple Teflon tape that is not shown in FIG. 12 for the purposes of brevity. Alternatively, any other type of covering means may be used to cover the lower portion of the inhaler 168 that extends outside the Inhaler Test Chamber. The fine groves are shown in the hand-held grip 170 of the Inhaler shown in FIG. 12.

As one example, if the No Colds, No Flus™ Inhaler is being tested, then the Inhaler contains 50% *Eucalyptus* Oil (*Eucalyptus globulus*) and 50% Tea Tree Oil (*Melaleuca alternifolia*). In this example, the vapor from this Inhaler is being tested to determine its effectiveness against anthrax. If the anthrax dies in the petri dish under the influence of the vapor from the Inhaler, then it would confirm the effectiveness of the vapor produced from a mixture of 50% *Eucalyptus* Oil and 50% Tea Tree Oil to eradicate anthrax.

The Inhaler Test Chamber 146 in FIG. 12 must be further isolated to contain dangerous test pathogens. Put another way, the Inhaler Test Chamber 146 must be entirely surrounded by another sealed safety chamber to contain the dangerous test pathogens. However, that additional isolation equipment is not shown for the purposes of brevity. Within this isolation equipment, a typical test is conducted as follows. First the test pathogens are grown on a pathogen growing medium in a petri dish which is then inserted through the access door into the Inhaler Test Chamber. Then the access door is closed. Then, the Test Inhaler 158 is inserted through grommet 160. The air inlet holes of the Inhaler are blocked off using Teflon tape or by using other means. The walls of the Inhaler Test Chamber may be made to be transparent. Then, the pathogens may be observed under the influence of the vapor from the essential oil within the Test Inhaler.

Other more complex Test Chambers may be assembled. When vapors from a typical Inhaler are inhaled into the lungs, and if sufficient vapor is inhaled, the vapor from the oil can actually "wet" the interior of the lungs. This "wetting" can be simulated as follows. A Flow Chamber covering the lower portion of the inhaler 168 that extends outside the Inhaler Test Chamber can be made and suitable attached to the wall of the Test Chamber adjacent to the Test Inhaler. That Flow Chamber is not shown in FIG. 12 in the interests of brevity. The pressure within the Flow Chamber (PFC) can be positively pressured with air with respect to the pressure within the Inhaler Test Chamber (PITC). If the air inlet holes of the Test Inhaler are open, then moist vapor is blown into the Inhaler Test Chamber through the vapor outlet orifice 62. The exhaust from the Inhaler Test Chamber may be accumulated from a pipe exiting the Inhaler Test Chamber and re-injected into the air input of the Flow Chamber keeping dangerous pathogens within a closed, continuously, circulating system. Then, the test pathogens in the petri dish may be observed and the effectiveness of the "wet" vapor from the essential oil may be determined.

Advantages of Inhaled Antiseptics to Prevent, Treat and Cure Respiratory Diseases Including SARS, the Bird Flu, and Potentially Unknown or Unidentified Infections Regretfully, there seems to be a fundamental reluctance in the medical community to test natural substances to prevent, treat, and cure human diseases despite the fact that many of our current drugs derive directly from natural substances such as taxol, aspirin, and penicillin—to name just a few. Despite this situation, there are intrinsic advantages to the new method of using inhaled antiseptic vapors, such as vapors from selected essential oils, to prevent, treat, and cure infections causing SARS. These intrinsic advantages are listed as follows:

A. From Ser. No. 09/542,703, and later, from Inouye, et al., 2001, selected essential oil vapors are known to be effective against certain infectious respiratory bacteria.

B. From the literature, liquid essential oils are known to have broad antiseptic properties against a wide variety of viruses, bacteria, and fungi.

C. Selected essential oil vapors are safe to inhale. For example the applicants are not aware of any known deaths cited in the medical literature from inhaling the vapors from *Eucalyptus globulus* ("*Eucalyptus* Oil").

D. Using essential oil vapors as inhaled antiseptics would be effective against combinations of viruses, bacteria and perhaps fungi that could form associated, or symbiotic relationships, resulting in complex infections that might be responsible for SARS.

E. An inhaled antiseptic approach is ideal when the nature of the pathogen is unknown and/or the pathogen mutates rapidly.

F. The essential oil vapors can be provided immediately to humans in the form of simple hand-held inhaler devices (such as those manufactured by Inhalation, Inc. at the web site of www.NoColds-NoFlus.com).

G. Most essential oils are fat soluble. Therefore, these oils permeate the lung tissue.

H. After inhalation, some of the vapors enter the blood stream. These oils are thought to cross the blood-brain boundary and may possibly eradicate pathogens elsewhere in the body.

I. According to the literature, there is little chance for humans overdosing on inhaling essential oil vapors. In about 2 hours after inhalation, the vapors have normally been exhaled back out of the body—primarily from the lungs.

J. Selected essential oils, such as *Eucalyptus* Oil, smell very good to humans, and the patients are therefore likely to repetitively inhale the vapors to suitably prevent, treat, or cure infections from pathogens causing SARS. It is likely necessary to repetitively inhale the essential oil vapors every 2 hours or so to prevent infections caused by a nearby infected individual who may be coughing, sneezing, etc.

K. Infections of pathogens causing SARS may be made more severe in the presence of other infections such as bronchitis, TB, or some other form of pneumonia in the patient. Therefore, a broad antiseptic approach is desirable.

L. If such an inhaled antiseptic approach appeared to "help", it could be implemented immediately giving more time to come up with other therapies, perhaps including immunization therapies.

M. Inhaled antiseptic essential oil vapors have an immediate impact in the lungs, whereas digested pills take relatively longer, and immunization can still take longer periods of time.

N. One of the co-inventors, William Banning Vail III, has been repetitively inhaling essential oil vapors from *Eucalyptus globulus* and *Melaleuca alternifolia* for about 3½ years as of the filing of Ser. No. 10/429,077. He has not had any lung infections during this period, and others have had similar experiences for about 2½ years (as of the Filing Date of Ser. No. 10/429,077). See "Our "Stories" on the web site of www.NoColds-NoFlus.com (or at www.InhalationProducts.com). Many M.D.'s and N.D.'s recommend inhaling the vapors from *Eucalyptus globulus* for other reasons, and please see their comments in the "References" on the cited web site.

O. Inhalers having essential oil vapors could at least provide a "first defense" to prevent the infection of pathogens causing SARS. The CDC web site has recently stated that surgical masks do not provide positive protection against either SARS, or against TB. Accordingly, the inhalers containing essential oils should be considered ASAP—particularly if SARS is caused by an airborne pathogen as suggested by some experts.

P. Each natural essential oil has many constituents—which are all well documented in the literature. If the vapors from natural essential oils are found to be effective against SARS, then perhaps the most effective ingredient, or combination of ingredients, can be rapidly isolated.

Q. Mankind has probably used *Eucalyptus* Oil and Tea Tree Oil for a broad range of respiratory conditions for many centuries. Perhaps these oils have additional uses which have yet to be confirmed by medical science. Please consider the history of aspirin as an analogy. There are also many other essential oils which can be considered that are listed in the above "List of Essential Oils".

R. *Eucalyptus* Oil is now used as a major active ingredient in Listerine (R). Tea Tree Oil is now used as the major antipathogenic ingredient in some toothpastes, mouthwashes, and in some shampoos.

S. During the evolutionary history of life on Earth, on Earth, essential oils in plants and trees have been theorized to have co-evolved with viruses, bacteria and fungi to protect the plants and trees from viral, bacterial and fungal infections. Accordingly, it seems wise to test these natural substances ASAP under the circumstances.

Inhalation, Inc

The inventors have formed Inhalation, Inc. to commercialize their inventions. As of this date, this firm manufactures and provides the following inhalers:

The No Colds, No Flus™ Personal Lung Inhaler that contains 100% *Eucalyptus globulus* ("*Eucalyptus* oil"). This may also be re-labeled to read "1st Inhalation Defense™".

The No Sinus Pain™ Personal Lung Inhaler that contains a mixture of *Eucalyptus globulus* ("*Eucalyptus* oil") and *Melaleuca alternifolia* ("Tea Tree oil"). This may also be re-labeled to read "2nd Inhalation Defense™".

The Wild Radiata™ Personal Lung Inhaler that contains 100% *Eucalyptus radiata* that is wild-picked in Australia. This may also be re-labeled to read "3rd Inhalation Defense™".

The Super Sinus & Lungs™ Personal Lung Inhaler that contains a mixture of *Eucalyptus globulus, Eucalyptus citriodora*, and *Melaleuca alternifolia*. This may also be re-labeled to read "4th Inhalation Defense™".

The No Asthma Attack™ Personal Lung Inhaler that contains *Eucalyptus radiata.*

The No Head Ache™ Personal Inhaler that contains a mixture of *Lavandula hybrida* ("Lavandin"), *Metha piperita* ("Peppermint") and *Betula alleghaniensis* ("Birch").

The No Stress, No Nerves™ Personal Inhaler that contains a mixture of *Lavandula angustifolia* ("Lavender oil") and *Eucalyptus globulus* ("*Eucalyptus* oil")

The Women's Hormone Balance™ Personal Inhaler that contains a mixture of *Citrus aur. bergamia* ("Bergamot"), *Salvia sclarea* ("Clary Sage"), and *Pelargonium roseum* ("Rose Geranium").

The Go To Sleep™ Personal Inhaler that contains a mixture of *Lavandula vera* ("Lavender oil") and *Anthemis nobilis* ("Roman Chamomile").

The Flu Away™ Personal Inhaler that contains a mixture of *Eucalyptus globulus* ("*Eucalyptus* oil") and *Melaleuca alternifolia* ("Tea Tree Oil").

The Lung Power™ Personal Inhaler that contains *Mentha piperita* ("Peppermint oil").

The Stop Nauseam™ Personal Inhaler that contains *Mentha piperita* ("Peppermint oil").

The Energizing™ Personal Inhaler that contains *Citrus aurantifolia* ("Lime"), *Citrus paradisi* ("Grapefruit"), *Citrus reticulata* ("Mandarin"), and *Citrus arantium* ssp. *bergamia* ("Bergamot").

The Immune Boost™ Personal Inhaler that contains *Thymus vulgaris* ("Thyme"), *Mentha piperita* ("Peppermint"), *Citrus limon* ("Lemmon"), *Melaleuca alternifolia* ("Tea Tree Oil"), *Melaleuca quinquenervia* ("Niaouli"), *Eucalyptus globulus* ("*Eucalyptus* Oil"), and *Syzygium aromaticum* ("Clove").

The Mental Clarity™ Personal Inhaler that contains *Citrus aurantifolia* ("Lime"), *Citrus paradisi* ("Grapefruit"), *Citrus sinensis* ("Sweet Orange"), and *Citrus aurantium* ssp. *bergamia* ("Bergamot").

The Men-O-Pause™ Personal Inhaler that contains *Pelargonium graveolens* ("Geranium"), *Foeniculum vulgare* ("Fennel"), *Salvia officinalis* ("Sage"), *Ocimum basilicum* ("Basil"), *Chamaemelum nobile* ("Roman Chamomile"), and *Cupressus sempervirens* ("Cypress").

These Inhalers are a commercial success. They are now sold on the internet and in high-end naturopathic stores. Several physicians are now using these inhalers in their normal practices.

Please also refer to selected Trademarks that include No Hot Flash™, No Menopause™, No Night Sweats™, No PMS™, No Toss, No Turn™, No Insomnia™, Aphrodesica Orgasmia™ (for an aphrodisiac essential oil), Love Potion No. 7®, Love Potion No. 8®, Love Potion No. 9®, and Love Potion No. 99 (the latter four also being appropriate for additional aphrodisiac oils).

The long-term use of the vapors from just one essential oil, like *Eucalyptus* Oil (in the No Colds, No Flus™ Inhaler), could hypothetically result in an immunity build-up of pathogens to this oil. Alternating another oil, such as the *Eucalyptus*-Tea Tree Oil Mix (in the No Sinus Pain™ Inhaler) can help prevent this. Rotating the use of inhaled vapors from multiple essential oils to prevent the build-up of immunity to the pathogens is also a preferred embodiment of the inventions disclosed in the above pending U.S. patent applications and in other relevant documents.

Any of the above listed essential oils, or any combination thereof, may be used for "lifestyle" purposes. The inhalers themselves may be used for medicinal proposes in the above patents and patent applications, or as lifestyle products.

Various embodiments of the invention provide improvements of the Inhalers for medicinal purposes and for lifestyle purposes. Several of these improvements are listed as follows:

A. The Crossbar: The crossbar built internally within the Inhaler Body prevents children from sucking the cotton out of the Inhaler. This is an important safety feature, because relatively small amounts of *Eucalyptus globulus* has been known to cause deaths in children. For example, see the safety data on the web site of www.InhalationProducts.com. To the knowledge of the inventors, there has been no Inhaler provided that uses 100% pure plant based essential oils for inhalation which also provides this crossbar for protection.

B. Fire Protection: Hospitals have been reluctant to use essential oils because of fire hazard. Often, diffusers are used that can produce dangerous fumes. Similarly, cotton balls soaked with essential oils are an extreme hazard in hospitals. Therefore, the invention provides an unanticipated benefit: namely it provides a practical way for patients within hospitals to use essential oil vapors while minimizing any fire hazard. These Inhalers are ideal to use on airplanes where the fire hazard of using diffusers or cotton balls soaked with essential oils are totally unreasonable. These Inhalers can be used in any public place or in any home to minimize the fire hazard from using essential oils.

C. Good Seals on Inhalers: The Inhalers have been designed to prevent any appreciable leaks around the sealing joints in the following locations: (a) cap-body; and (b) plug-body. This is very important. With leaky fitting parts, the most volatile components leak from the Inhaler first. Therefore, after sufficient leaking, the vapors are not representative of the essential oil being used for medicinal or lifestyle purposes.

D. Dosage: Hospitals have found that patients using cotton balls soaked with essential oils provide very irregular doses to patients. The Inhaler provides a means to provide repetitive controlled doses of essential oil vapors to patients.

E. Inhalers to Help Nausea: In another preferred embodiment of the invention, the vapors from the essential oils of peppermint, ginger, and spearmint are inhaled by patients to help with nausea. One of the inventors used such an inhaler to minimize the nausea following a hernia operation and it worked.

Coffee Bean Inhalers

Figure 13:
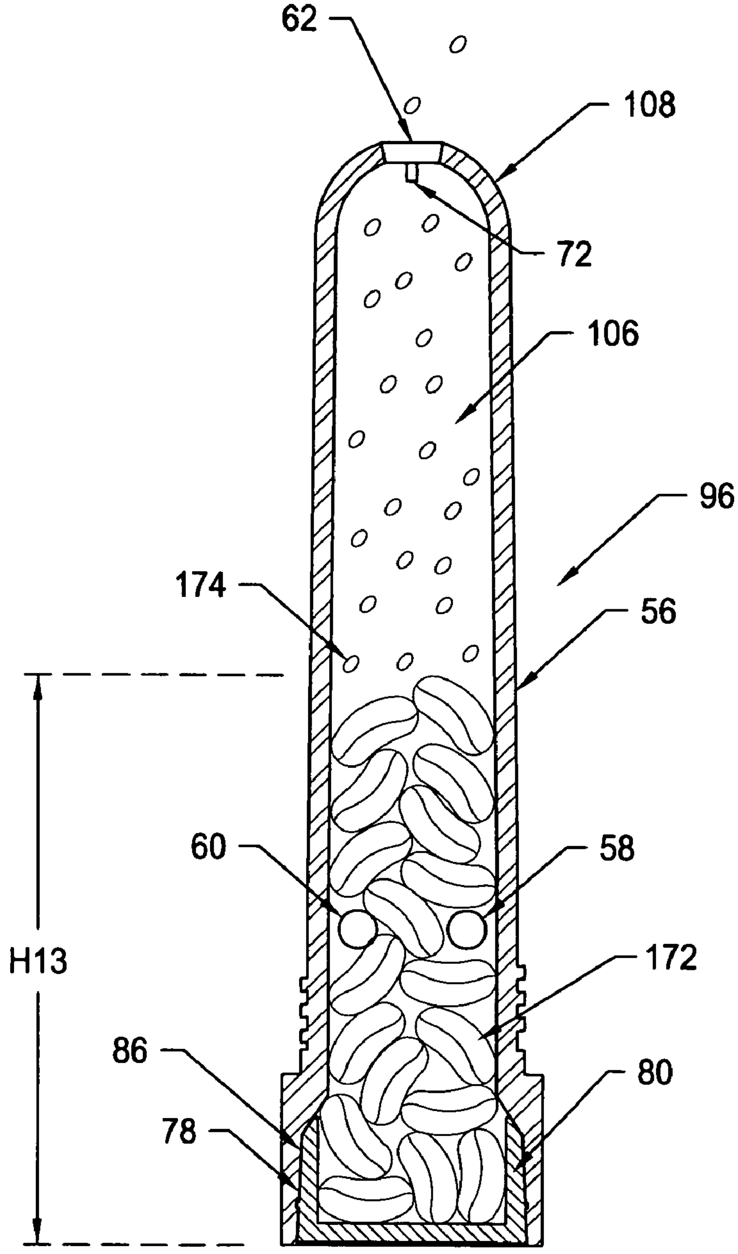
FIG. 13 shows a cross section of an assembled Inhaler having one type of coffee bean in the Inhaler.

In FIG. 13, all the numerals have been previously defined except for the following. Inhaler Body 56 contains roasted coffee beans. In FIG. 13, all the coffee beans are of the same type. For example, all the coffee beans in FIG. 13 may be French Roast coffee beans. Numeral 172 shows one such roasted coffee bean. The oils within the roasted coffee beans and on their surface produce a vapor within the body of the Inhaler. Representative of that vapor is element 174 in FIG. 13. This vapor is comprised of the volatile components of the oils within and on the surface of the roasted coffee beans. The tip of the assembled Inhaler 108 is placed near to, or inside, a nostril of the nose so that the volatile vapors from the coffee beans may be inhaled. The beans are filled to a height of H13. In FIG. 13, there are number N13 coffee beans within the Inhaler Body collectively weighing a total mass of M13 grams, a fraction F13 of which is the mass of coffee bean oils. The aroma produced is approximately proportional to the following quantity: {(M13)(F13)}.

The oils within the coffee beans are affected by the type of beans and by the roasting process. Typical coffee is affected by blending of the various beans and by the brewing process. Typical constituents of coffee and coffee bean oils include phenolic polymers, polysaccharides, chlorogenic acids, minerals, water, caffeine, organic acids, sugars, lipids, aromatic compounds, and quinolactones (quinides) (from the Institute for Coffee Studies and Vanderbilt University Medical Center at http://www.mc.vanderbilt.edu/coffee/chemical.html.) The volatile constituents of these compounds are inhaled from the tip of the hand-held Inhaler shown in FIG. 13.

A total of 5 prototype hand-held Inhalers were assembled on Tuesday, Aug. 19, 2003 as shown in FIG. 13. These Inhalers had coffee beans in them. Three of them had decaffeinated coffee beans in them. Two of them had caffeinated coffee beans is them. These beans were "French roasted" beans and were made by Millstone®.

Coffee beans have natural oils on them that produce a vapor that is inhaled from the Inhalers. When W. Banning Vail Ph.D. inhaled from the Inhaler having roasted caffeinated coffee beans, he got an immediate pleasant sensation and a stimulative "jolt". It acted as an immediate stimulant and caused an immediate sensation being "extremely wide-eyed awake". This gave W. Banning Vail, Ph.D. a typical "coffee jolt". This "jolt" is extremely useful when trying to wake up in the morning. This type of Inhaler can be extremely useful to individuals who need to be alert such as airline pilots, people who are studying, etc. Further many people do not like to drink coffee, but do enjoy the aroma from coffee. This type of Coffee Bean Inhaler shown in FIG. 13 is an ideal for such individuals. This experiment was done in private, and was not a public demonstration.

W. Banning Vail, Ph.D. also got a mild stimulative reaction from the decaffeinated beans in the Inhaler. He drinks coffee often, and perhaps the aroma itself of coffee helps produce such a psychological reaction.

Marilyn L. Vail and W. Banning Vail, Ph.D. had previously invented the Coffee Bean Inhaler. We hereby trademark the name Coffee Bean Inhaler™. Although many Coffee Bean Inhalers™ will use roasted coffee beans, other preferred embodiments contemplate using coffee beans processed in different manners.

Marilyn L. Vail, and W. Banning Vail, III all very much liked the prototype Coffee Bean Inhalers. This experiment was done in private, and was not a public demonstration.

Experience has shown that the off-the-shelf-life of these Inhalers is at least several months. Natural beans are best if fresh, i.e., before any spoilage of any type. One cause of spoilage would be due to bacteria, viruses, or fungi attacking the beans within the Inhaler. If that eventually proves to be an undesirable problem, then radiating the beans or the Inhalers with gamma rays, or the like, can be used to sterilize the beans to increase the shelf life. Any method to sterilize the coffee beans to increase their shelf-life that does not interfere with the aroma or chemicals present in the beans are acceptable. Our tightly sealed Inhalers will extend the shelf life.

Two more prototype Inhalers were assembled on Thursday, Aug. 21, 2003. One was completely full of French Roast beans from Starbucks®. Another was about ⅔ full of French Roast beans from Starbucks. These French Roast beans were caffeinated coffee beans. Similar comments apply to these Inhalers as to the above. The intensity of the aroma from the beans depends upon the number of beans in each Inhaler. The more beans, the stronger the aroma. This experiment was done in private, and was not a public demonstration.

The natural oils within the beans may be suitably vapor distilled or otherwise obtained. The essential oils from coffee beans may also be suitably obtained. Then the Inhalers may be assembled using normal cotton inserts dipped into this coffee bean essential oil as shown in FIGS. 1-11. The whole beans are not inhaled thorough the protective "cross bar" of the Inhaler, and are therefore safe.

Ground coffee directly inserted in the Inhaler without an additional screen might be inhaled into the lungs. But a suitable screen or other containment means within the Inhaler would allow the use of ground coffee beans. As an example, element 122 in FIGS. 8, 9, and 10 may be replaced with a very fine screen, or other suitable filter with small pores, so that the ground coffee may be safely used in the Inhaler and the resulting vapors safely inhaled by users.

Such apparatus and methods as described herein may be used to test for the aroma produced from coffee beans by manufacturers of coffee or buyers of coffee beans. In a warehouse full of coffee, placing a few beans in the Inhaler apparatus and then inhaling through the nostril will give a clear indication of the true aroma of the beans in the Inhaler that is relatively unaffected by the aroma produced by adjacent bags of coffee beans in the warehouse.

Figure 14:
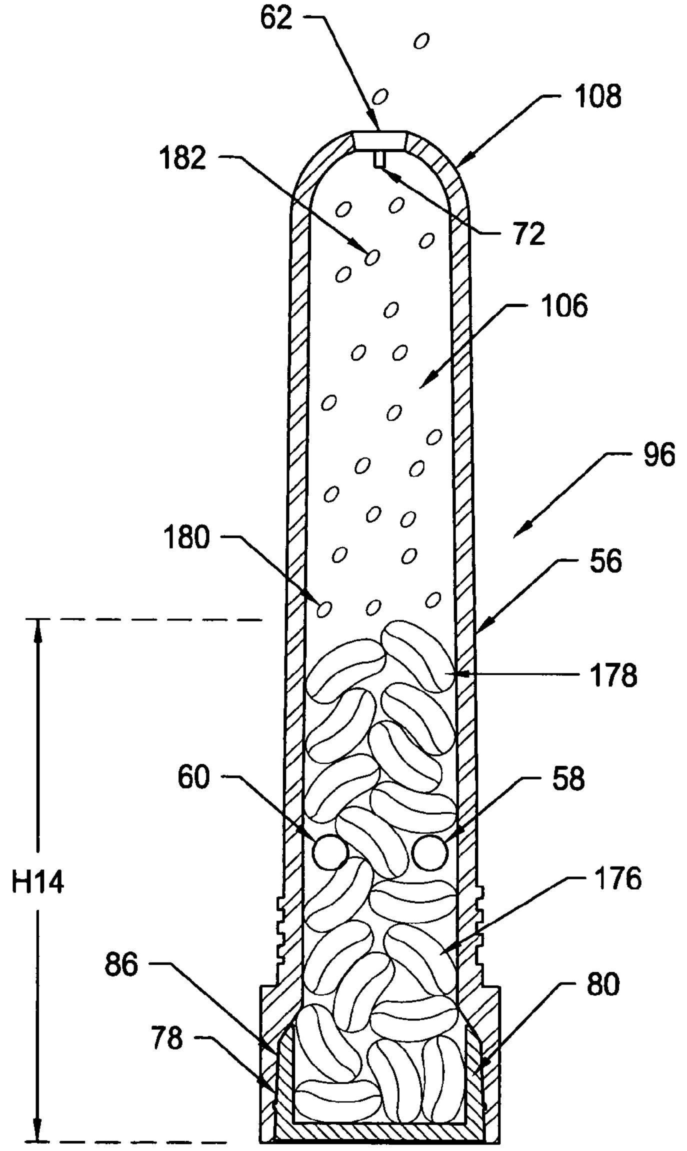
FIG. 14 shows a cross section of an assembled Inhaler having two types of coffee beans in the Inhaler.

In FIG. 14, all the numerals have been previously defined except for the following. Inhaler Body 56 contains roasted coffee beans. In FIG. 14, there are more than one type of coffee beans in the Inhaler Body. Numeral 176 shows one such roasted coffee bean and numeral 178 shows another such coffee bean. The oils within the roasted coffee beans and on their surface produce a vapor within the body of the Inhaler. Representative of that vapor is element 180 emitted from the type of coffee beans designated as element 176. Also representative of that vapor is element 182 emitted from the type of coffee beans designated as element 178 in FIG. 14. The combined aroma of the different vapors within the Inhaler Body produce an aroma that is indicative of the mixture of coffee beans within the Inhaler. This vapor is comprised of the volatile components of the oils within and on the surface of the roasted coffee beans. The tip of the assembled Inhaler 108 is placed near to, or inside, a nostril of the nose so that the volatile vapors from the coffee beans may be inhaled. The beans are filled to a height of H14. In FIG. 14, there are number N14A coffee beans of the type representative by element 176 within the Inhaler Body collectively weighing a total mass of M14A grams, a fraction F14A of which is the mass of the related coffee bean oils. In FIG. 14, there are number N14B coffee beans of the type representative by element 178 within the Inhaler Body collectively weighing a total mass of M14B grams, a fraction F14B of which is the mass of the related coffee bean oils. In FIG. 14, and at a given temperature, the aroma produced is approximately proportional to the following quantity: {(M14A)(F14A)+(M14B)(F14B)}. In principle, any number of different types of coffee beans may be located within the interior of the Inhaler shown in FIG. 14.

Another preferred embodiment includes a new method of doing business that relates the sales of coffee in a coffee shop such as Starbucks® to the sales of Coffee Bean Inhalers™ having selected beans that are ground to make the coffee sold by Starbucks. For example, under "Mild" blends, Starbucks provides the "Starbucks® Breakfast Blend", the "Lightnote Blend®", the "Decaf Lightnote Blend®", the "House Blend", the "Decaf House Blend" and the "Colombia Narino Supremo" blend. As another example, under "Smooth" blends, Starbucks® provides the "Guatemala Antigua" blend, the "Yukon Blend®", the "Caffe Verona®" blend, the "Expresso Roast" blend, the "Decaf Expresso Roast" blend, the "Arabian Mocha Java" blend, and the "Decaf Mocca Java" blend. As yet another example, under "Bold" blends, Starbucks® provides the "Ethiopia Sidamo" blend, the "Kenya" blend, the "Arabian Mocha Sanani" blend, the "Sumatra" blend, the "Decaf Sumatra" blend, the "Sulawesi" blend, the "French Roast" blend, the "Italian Roast" blend, and the "Gold Coast Blend®". The above is quoted from a pamphlet found at a Starbucks coffee shop entitled "The World of Coffee" and "A Guide to Starbucks™ Whole Bean Selections" that is "SKU #177852".

As an example of a new method of doing business, Starbucks may decide to give away one Inhaler with the French Roast blend with each such cup of coffee it sells as a promotion. Then when the customer is away from the coffee shop, the customer may inhale the vapors from the French Roast blend as reminder to visit the coffee shop again.

Yet another preferred embodiment of the invention is to provide a wide variety of different Coffee Bean Inhalers with the different beans available from Starbucks®. Therefore, for each bean sold by Starbucks, there could be a corresponding Coffee Bean Inhaler™. A rack of such Inhalers could be placed on a typical counter within a Starbucks store. Similar comments apply to other manufacturers of coffee beans.

There is an alternative use for such Inhalers. When William Banning Vail III inhaled vapors from the Inhaler containing French Roast described earlier, he was able to reduce the number of cups of coffee consumed. The vapors from the Inhaler seemed to satisfy his "need" for additional cups of coffee. So, the method of using the inhaled vapors from coffee beans to reduce the craving for coffee is a new use for the Inhalers.

In view of the above disclosure, a preferred embodiment of the invention is a method of inhaling vapors from coffee beans within a hand-held inhaler apparatus to stimulate the human body.

In view of the above disclosure, another preferred embodiment of the invention is a method of inhaling vapors from the oils within the interior and on the surface of roasted coffee beans contained within a hand-held inhaler apparatus to stimulate the human body.

In view of the above disclosure, yet another preferred embodiment of the invention is a method of inhaling vapors from the essential oil obtained from coffee beans from a hand-held inhaler apparatus to stimulate the human body.

In view of the above disclosure, yet another preferred embodiment of the invention is a hand-held inhaler apparatus to provide the aroma from coffee beans for human inhalation through a nostril for testing the aroma from the coffee beans.

And finally, in view of the above disclosure, another preferred embodiment of the invention is the method of inhaling vapors from the oils within the interior and on the surface of roasted coffee beans contained within a hand-held inhaler apparatus to reduce the desire for a cup of coffee.

Inhalers for Nausea Caused by Chemotherapy

The Stop Nausea™ Inhaler now in production by Inhalation, Inc. has proven to be successful in preventing, treating, and curing the symptoms of nausea caused by chemotherapy treatments of human cancers. A cross section of a preferred embodiment of the Inhaler is shown in FIG. 5. In one preferred embodiment of this Inhaler, the pure the cotton insert 98 in FIG. 5 has been soaked in the essential oil from *Mentha piperita*. The common name for the essential oil from *Mentha piperita* is "peppermint oil". In FIG. 5, the essential oil 100 is chosen to be the essential oil from *Mentha piperita*.

An individual, known by his initials as L. W., was being treated for cancer with cancer a little over one year ago. He successfully overcame his cancer. He was not responding to the standard anti-nausea medication provided to him by his physicians. This standard medication included taking expensive pills that he said cost about $40 each, and which did not work at all for him. If the nausea had already begun following chemotherapy, he found that inhaling deeply from the Stop Nausea Inhaler would cause the nausea to stop within 30 seconds to 2 minutes after deep inhalation through a nostril. Inhaling from the Stop Nausea Inhalers before a chemotherapy session prevented the onset of Nausea.

A major surgical hospital in the state of Washington has used the Stop Nausea Inhaler to good effect. In 8 of 10 patients complaining about post-operative nausea, deeply inhaling from the Stop Nausea Inhaler caused post-operative nausea to stop within 30 seconds to 2 minutes after inhalation. This is a very high success rate.

Following my own hernia operation, I used a prototype of the Stop Nausea Inhaler to stop my nausea following my operation during February of 2003.

Another individual, known by her initials as M. E. T., has also used our inhalers with great success. She also found that inhaling vapors from the Stop Nausea Inhaler caused any nausea to stop within 30 seconds to 2 minutes after inhalation. She also found that deeply inhaling the vapors from the Stop Nausea Inhaler immediately before a chemotherapy session and often prevented the onset of nausea during the following two hour period.

M. E. T. also used our No Stress, No Nerves™ Inhaler to reduce anxiety before the onset of a chemotherapy session. The No Stress, No Nerves Inhaler possesses the essential oil from *Lavandula angustifolia*. Vapors from this essential oil reduces anxiety, reduces stress, and calms the nerves before a chemotherapy session. On many occasions, M. E. T. also inhaled vapors from the No Stress, No Nerves Inhalers approximately 20 minutes before a chemotherapy session to reduce stress. She then inhaled vapors from the Stop Nausea Inhaler about 5 minutes before the chemotherapy session to prevent the onset of nausea. The two inhalers used in this combination reduces stress and prevents nausea.

The Inhaler apparatus shown in FIG. 5 is ideal for use by chemotherapy patients for reasons including the following:

1. The Inhaler apparatus allows each patient to determine a self-controlled dose of vapors to be inhaled that is adequate to prevent, treat or cure nausea caused by chemotherapy. This dose may be repeated by the patient. By contrast, if a cotton ball is soaked with peppermint oil, and the vapors are inhaled, it is very difficult to obtain a repeatable dose of peppermint oil vapors.

2. Peppermint oil is flammable. In some situations, it would be tempting to inhale peppermint oil vapors from a cotton ball soaked in peppermint oil. However, having open bottles of peppermint oil, and cotton balls soaked with peppermint oil, provides a significant fire hazard. So, using cotton balls soaked with peppermint oil in operating rooms and in other portions of a hospital presents an unacceptable fire hazard. Using the tightly sealed Inhalers would prevent the possibility of spilling the peppermint oil on the operating room floor, on a hospital floor, or otherwise exposing open cotton balls soaked with peppermint oil to the possibility of ignition. The Inhalers have been very carefully designed to have very tight seals to prevent any escape of the vapors when the Cap is on the Inhaler. The "flash point" of peppermint oil is 65 to 68 degrees C. according to the "Material Safety Data Sheet" of the firm identifying itself as "Sargent-Welch" (and VWR International) on the internet at www.sargentwelch.com (on the date of Nov. 14, 2004). The "flash point" is the lowest temperature at which a liquid can form an ignitable mixture in air near the surface of the liquid.

3. Using the Inhaler apparatus in FIG. 5 provides an individual the ability to inhale just the vapors needed for his/her own needs. Cotton balls soaked with peppermint oil in the hospital environment, and in other crowded environments, exposes others to peppermint oil vapors. Although relatively rare, some individuals are allergic to the vapors from peppermint oil. So, the Stop Nausea™ Inhaler is used to provide just the vapors to the individual that is needed by the individual to prevent, treat, or cure nausea, and does not needlessly expose others to these vapors.

4. The Stop Nausea Inhaler may be used to save money at hospitals. If a patient becomes nauseous, then the staff must devote time and effort to overcome this nausea. Furthermore, the No Stress, No Nerves Inhaler may also be used to save money at hospitals during chemotherapy by reducing the fear and stress on patients. When patients are fearful, they are not as cooperative, and costs the hospital time.

The effective amount, or effective dose, of vapors from the vaporized essential oil from *Mentha piperita* ranges between 0.1 micrograms to 50 micrograms of vaporized essential oil, and varies from individual to individual. The minimum effective dose also varies depending upon the length of time that the dose is to be effective. Put another way, more essential oil vapors must be inhaled to prevent the return of nausea for 2 hours, than to prevent the return of nausea for 15 minutes. However, a typical effective amount, or typical effective dose, of vaporized essential oil from *Mentha piperita* is 11 micrograms of vaporized essential oil. The density of *Mentha piperita* at room temperature is typically 0.89 grams per milliliter.

The particular essential oil from *Mentha piperita* has been carefully chosen so that it can be deeply inhaled. The essential oil is a first distillation essential oil from a steam distillation process. It is certified not to contain any pesticides nor heavy metals. It is grown organically, and has a chemical constituency allowing for deep inhalation of the vapors from *Mentha piperita*. Non-organically grown, and inexpensive peppermint oils, are very harsh when inhaled. These harsh oils are not ideal for preventing treating, or curing chemotherapy induced nausea.

In view of the above disclosure, a preferred embodiment of the invention is a method to treat nausea during a chemotherapy session for human cancers comprising at least the following steps:

(a) after a first particular time period during the chemotherapy session after which nausea has developed, deeply inhaling a first effective amount of concentrated vapors of the essential oil from *Mentha piperita* from a hand-held inhaler apparatus;

(b) thereafter, waiting a second time period of 30 seconds to 2 minutes for the chemotherapy induced nausea to stop;

(c) thereafter, in the event that nausea returns during the remainder of the chemotherapy session, deeply inhaling a second effective amount of vapors from the essential oil from *Mentha piperita* periodically not more often than a third time period of every 15 minutes;

(d) after the completion of the chemotherapy session at the end of a fourth time period, and in the event that nausea thereafter returns, inhaling a third effective amount of vapors from the essential oil from *Mentha piperita* not more often than a fifth time period of every 1 hour.

Also disclosed is the above method wherein the first, second, and third effective amounts are equal. Also disclosed is the above method wherein the first, second, and third effective amounts are equal to 11 micrograms of the vaporized essential oil from said *Mentha piperita*. Also disclosed is the above method wherein the first, second, and third effective amounts are not equal.

In view of the above disclosure, another preferred embodiment of the invention is a method to prevent nausea during a chemotherapy session for human cancers comprising at least the following steps:

(a) in a first time period of 10 minutes in advance of the chemotherapy session, deeply inhaling from a hand-held apparatus an effective amount of vapors from the essential oil from *Mentha piperita;*

(b) until the chemotherapy session ends, deeply inhaling the effective amount periodically every second time period of time of 15 minutes until said chemotherapy session has ended.

Also disclosed is the above method wherein said effective amount of said vapors from said essential oil from *Mentha piperita* is equal to 11 micrograms of vaporized essential oil.

In view of the above disclosure, another preferred embodiment of the invention is a method to save time in advance of a chemotherapy session for human cancers in a hospital that includes at least the following steps:

(a) from a first hand-held apparatus, deeply inhaling a first effective amount of the vapors from the essential oil from *Mentha piperita* to prevent the onset of chemotherapy induced nausea; and (b) from a second hand-help apparatus, deeply inhaling a second effective amount of the vapors from the essential oil from *Lavandula angustifolia* to reduce anxiety; whereby the prevention of said nausea and the reduction of said anxiety saves time of medical providers in a hospital environment.

In view of the above disclosure, another preferred embodiment of the invention is a method to treat nausea during, and after, a chemotherapy session for human cancers comprising at least the step of deeply inhaling an effective amount of vapors from the essential oil from *Mentha piperita.*

In view of the above disclosure, yet another preferred embodiment of the invention is a method to prevent nausea before a chemotherapy session for human cancers comprising at least the step of deeply inhaling an effective amount of vapors from the essential oil from *Mentha piperita.*

Other essential oils may be used in the Inhaler apparatus shown in FIG. 5 to prevent, treat, or cure nausea. Those essential oils include ginger and spearmint as well (common names used here). Any essential oil in the above List of Essential Oils that are used to prevent, treat, or cure chemotherapy induced nausea are different preferred embodiments of this invention.

REFERENCES

The above recited references are defined as follows, entire copies of which are incorporated herein by reference:

Alibek, K. W., and Handelman, S., the book entitled "Biohazard: The Chilling True Story of the Largest Covert Biological Weapons Program in the World", Dell Publishing Company, 2000 ("Alibek and Handelman, 2000")

Alstat, E., the paper entitled "Lomatium Dissectum, An Herbal Virucide", in the journal called "Complementary Medicine", May/June 1987, pages 32-33 ("Alstat, 1987") [Ed Alstat]

Anderson, K. N., Anderson, L. E., and Glanze, W. D., Editors, the book entitled "Mosby's Medical Dictionary", Fourth Edition, Mosby-Year Book Inc., St. Louis, Mo., 1994 ("Anderson, et al., 1994")

Arnon, S. S., in the article entitled "Botulinum Toxin as a Biological Weapon, Medical and Pubic Health Management", Journal of the American Medical Association, Vol. 285, No. 8, Feb. 28, 2001, pages 1059-1070 ("Arnon, 2001") [Stephen S. Arnon, M.D.]

Audesirk, T., and Audesirk, G., the book entitled "Biology, Life on Earth", Fourth Edition, Prentice Hall, Upper Saddle River, N.J., 1996 ("Audesirk and Audesirk, 1996") [Teresa Audesirk and Gerald Audesirk]

Balch, J. F., and Balch, P. A., the book entitled "Prescription for Nutritional Healing", Second Edition, Avery Publishing Group, Garden City Park, New York, N.Y., 1997 ("Balch and Balch, 1997") [James F. Balch, M.D. and Phyllis A. Balch, C.N.C.]

Balch, J. F., and Balch, P. A., the book entitled "Prescription for Nutritional Healing", Third Edition, Avery Publishing Group, Garden City Park, New York, N.Y., 2000 ("Balch and Balch, 2000") [James F. Balch, M.D. and Phyllis A. Balch, C.N.C.] (was old Reference 7 in PPA-2)

Berkow, R., and Beers, M. H., Editors, the book entitled "The Merck Manual of Medical Information", "Home Edition", Pocket Books, a Division of Simon & Schuster, Inc., New York, N.Y., 1997 ("Berkow and Beers, 1997") [Robert Berkow, M.D. and Mark H. Beers M.D.]

Beers, M. H., and Berkow R., Editors, the Publication on the World Wide Web (http://www.merck.com/pubs/mmanual/) entitled "The Merck Manual of Diagnosis and Therapy", "Seventeenth Edition", "Centennial Edition", Merck & Co., Whitehouse Station, N.J., 1999 ("Beers, et al., 1999") [Mark H. Beers, M.D., and Robert Berkow, M.D.]

Borio, L., et al., the article entitled "Hemorrhagic Fever Viruses as Biological Weapons, Medical and Public Health Management", the Journal of the American Medical Association, Vol. 287, No. 18, May 8, 2002, pages 2391-2405 ("Borio, et al., 2002") [Luciana Borio, M.D.]

Buck, D. S., Nidorf, D. M., and Addino, J. G., the article entitled "Comparison of two topical preparations for the treatment of onychomycosis: *Melaleuca Alternifolia* (tea tree) oil and clotrimazole", in the Journal of Family Practice, Volume 38, No. 6, pages 601-605, 1994 ("Buck, et al., 1994")

Dennis, D. T., the article entitled "Tularemia as Biological Weapon, Medical and Public Health Management", Journal of the American Medical Association, Vol. 285, No. 21, Jun. 6, 2001, pages 2763-2773 ("Dennis, et al., 2001") [David T. Dennis, M.D., M.P.H.]

Editor, the book entitled "A Dictionary of Biology", Third Edition, Oxford University Press, New York, N.Y., 1996 ("Oxford, 1996")

Editor, the article entitled "Allergy, Asthma, and Sinus" on the World Wide Web (http://allergy-asthma-sinus.com/) dated Apr. 8, 2002 by the Allergy, Asthma and Sinus Resource Center, Miami, Fla. that was printed-out on Apr. 30, 2002, ("Allergy, Asthma and Sinus Resource Center, 2002")

Editor, in the document entitled "Common Infections" from the web site for the "Community Outreach Health Information Service" or "COHIS" (http://www.cohis.org) that was printed out on Apr. 30, 2002, ("COHIS, 2002")

Editor, the article entitled "Protein could beat cholesterol as indicator of heart risk" in the section entitled "Medical Digest", The Seattle Times, Mar. 24, 2000, page A7 ("The Seattle Times, 2000")

Editor, the article entitled "Sinusitis" on the World Wide Web Site entitled "drkoop.com", printed out on Apr. 30, 2002, ("DrKoop.com, 2002")

Editor, the article entitled "Sinusitis (Sinus Infection)" on the World Wide Web Site entitled "Medical College of Wisconsin Physicians & Clinics (http://www.healthlink.mcw.edu/), printed out on Apr. 30, 2002, ("Medical College of Wisconsin Physicians & Clinics, 2002")

Ellison, D. H., the book entitled "Handbook of Chemical and Biological Warfare Agents", CRC Press, 1999 ("Ellison, 1999")

Falkenrath, R. A., Newman, R. D., and Thayer, B. A., the book entitled "America's Achilles' Heel: Nuclear, Biological, and Chemical Terrorism and Covert Attack", MIT Press, 1998 ("Falkenrath, et al., 1998")

Fugh-Berman, A., the book entitled "Alternative Medicine, What Works", Williams & Wilkins, Baltimore, Md., 1997 ("Fugh-Berman, 1997") [Adriane Fugh-Berman, M.D.]

Gunther, E., the book entitled "The Essential Oils", Volumes I, II, III, and IV, Lancaster Press, Lancaster, Pa., 1948 ("Gunther, 1948")

Hedges, L. M. and Wilkens, C. L., the article entitled "Component Analysis of *Eucalyptus* Oil by Gas Chromatography-Fourier Transform-Infrared Spectrometry-Mass Spectrometry", in the publication called the Journal of Chromatographic Science, Volume 29, August, 1991 ("Hedges and Wilkens, 1991")

Henderson, D. A., in the article entitled "Smallpox as a Biological Weapon, Medical and Public Health Management", Journal of the American Medical Association, Vol. 281, No. 22, Jun. 9, 1999, pages 2177-2137 ("Henderson, 1999") [Donald A. Henderson, M.D., M.P.H.]

Horowitz, L. G., and Lindenbach, J. G., the book entitled "Death in the Air: Globalism, Terrorism and Toxic Warfare", Tetrahedron Publishing Group, 2001 ("Horowitz and Lindenbach, 2001")

Igram, C., the book entitled "Killed on Contact, The Tea Tree Oil Story: Nature's Finest Antiseptic", Literary Visions Publishing, Inc., Cedar Rapids, Iowa, 1992 ("Igram, 1992") [Cass Igram, D.O.]

Inglesby, T. V., et al., the article entitled "Plague as a Biological Weapon, Medical and Public Health Management", Journal of the American Medical Association", Vol. 283, No. 17, May 3, 2000, pages 2281-2290 ("Inglesby, et al. 2000") [Thomas V. Inglesby, M.D.]

Inglesby, T. V., et al., the article entitled "Anthrax as Biological Weapon, 2002, Updated Recommendations for Management", the Journal of the American Medical Association, Volume 287, No. 17, May 1, 2002, pages 2236-2252 ("Inglesby, et al., 2002") [Thomas V. Inglesby, M.D.]

Institute of Medicine, the book entitled "Chemical and Biological Terrorism Research and Development to Improve Civilian Medical Response", National Academy Press, 1999 ("Institute of Medicine, 1999")

Inouye, S., et al., the article entitled "Antibacterial activity of essential oils and their major constituents against respiratory tract pathogens by gaseous contact", Journal of Antimicrobial Chemotherapy (The British Society for Antimicrobial Chemotherapy), Volume 47, 2001, pages 565-573, 2001, ("Inouye, et al., 2001")

Jacobs, M. R., Hornfeldt, C. S., the article entitled "*Melaleuca* oil poisoning", in the journal called "Clinical Toxicology", Volume 32, No. 4, pages 461-464, 1994 ("Jacobs and Hornfeldt, 1994")

Kohn, L., Corrigan, J., and Donaldson, M., Editors, the book entitled "To Err is Human, Building a Safer Health System", "Advanced Copy", Institute of Medicine, National Academy Press, Washington, D.C., 1999 ("Kohn, et al., 1999") [Linda T. Kohn, Janet M. Corrigan, and Molla S. Donaldson]

Lawless, J., the book entitled "Tea Tree Oil", Harper Collins Publishers, Hammersmith, London, U.K., 1994 ("Lawless, 1994") [Julia Lawless]

Lawless, J., the book entitled "The Illustrated Encyclopedia of Essential Oils", Barnes & Noble Books, New York, N.Y., 1999 ("Lawless, 1999") [Julia Lawless]

Luckmann, J., Editor, the book entitled "Saunders, Manual of Nursing Care", W.B. Saunders Company, Philadelphia, Pa., 1997 ("Luckmann, 1997") [Joan Luckmann, MA, RN]

Mangold, T., and Boldberg, J., the book entitled "Plague Wars: The Terrifying Reality of Biological Warfare", Martin's Press, 2001 ("Mangold and Boldberg, 2001")

Martin, E., Ruse, M., and Holmes, E., Editors, the book entitled "A Dictionary of Biology", Third Edition, Oxford University Press, New York, N.Y., 1996 ("Martin, et al., 1996") [Elizabeth Martin MA; Michael Ruse BSc, PhD; and Elaine Holmes BSc, PhD]

Miller, J., Engelberg, S., and Broad, W. J., the book entitled "Germs: Biological Weapons and America's Secret War", Simon & Schuster, 2001 ("Miller, et al., 2001")

Miller, L., and Miller, B., the book entitled "Ayurveda & Aromatherapy, The Earth Essential Guide to Ancient Wisdom and Modern Healing", Lotus Press, Twin Lakes, Wis., 1995 ("Miller and Miller, 1995") [Dr. Light Miller, ND, and Dr. Bryan Miller, DC]

Moore, P., the book entitled "Killer Germs, Rogue Diseases of the Twenty-First Century", Carlton Books Limited, London, Great Britain, 2001 ("Moore, 2001") [Pete Morre B.Sc., Ph.D.]

Murray, M. T., the book entitled "Natural Alternatives to Over-the-Counter and Prescription Drugs", William Morrow and Company, Inc., New York, N.Y., 1994, ("Murray, 1994") [Michael T. Murray, N.D.]

Neufeldt, V., and Guralnik, D., the book entitled the Webster's New World™ Dictionary of American English, Third College Edition, Simon & Schuster, Inc., New York, N.Y., 1988 ("Neufeldt and Guralnik, 1988")

Olsen, C., the book entitled "Australian Tea Tree Oil Guide", Kali Press, Pagosa Springs, Colo., 1991, ("Olsen, 1991") [Cynthia B. Olsen]

Olsen, C., the book entitled "Australian Tea Tree Oil Guide", Third Edition, Kali Press, Pagosa Springs, Colo., 1997 ("Olsen, 1997") [Cynthia Olsen]

Osterholm, M. T., and Schwartz, J., the book entitled "Living Terror: What America Needs to Know to Survive the Coming Bioterrorist Catastrophe", Dell Publishing Company, 2001 ("Osterholm and Schwartz, 2001")

Price, S., and Price, L., the book entitled "Aromatherapy for Health Professionals", Second Edition, Churchill Livingstone, New York, N.Y., 1999 ("Price and Price, 1999") [Shirley Price and Len Price]

Regis, E., the book entitled "The Biology of Doom: The History of America's Secret Germ Warfare Project", Henry Holt & Company, 1999 ("Regis, 1999")

Rose, J., the book entitled "375 Essential Oils and Hydrosols", Frog, Limited, Berkeley, Calif., 1999 ("Rose, 1999") [Jeanne Rose]

Schnaubelt, K., the book entitled "Advanced Aromatherapy, The Science of Essential Oil Therapy", Healing Arts Press, a division of Inner Traditions International, Rochester, Vt., 1998 ("Schnaubelt, 1998") ["Kurt Schnaubelt, Ph.D."]

Schnaubelt, K., the book entitled "Medical Aromatherapy, Healing with Essential Oils", Frog, Ltd., Berkeley, Calif., 1999 ("Schnaubelt, 1999")

Sherry, E., and Warnke, P. H. H., the paper entitled "Alternative for MRSA and Tuberculosis (TB): *Eucalyptus* and Tea-Tree Oils as New Topical Antibacterials", Poster Board Number: P376, 2002 Annual Meeting of the American Academy of Orthopaedic Surgeons, Dallas, Tex., Feb. 13-17, 2002 ("Sherry and Warnke, 2002") [Eugene Sherry, M.D., and P. H. H. Warnke, Ph.D.]

Sullivan, J. B., Rummack, B. H., and Thomas, H., in the article entitled "Pennyroyal oil poising and hepatoxicity", in the Journal of the American Medical Association, Volume 242, No. 26, pages 2873-74, 1979 ("Sullivan, et al., 1979")

Swords, G. and Hunter, G. L. K., in the article entitled "Composition of Australian Tea Tree Oil (*Melaleuca alternifolia*)" presented in the Journal of Agricultural Food Chemistry, Volume 26, No. 3, 1978, pages 734-737 ("Swords and Hunter, 1978")

Taylor, E. R., the book entitled "Lethal Mists: An Introduction to the Natural and Military Sciences of Chemical, Biological Warfare and Terrorism", Nova Science, 1999 ("Taylor, 1999")

Tucker, J. B., in the book entitled "Toxic Terror: Assessing Terrorist Use of Chemical and Biological Weapons", MIT Press, 2000 ("Tucker, 2000")

Vallence, W. B., the article entitled "Pennyroyal poisoning: a fatal case", in the journal called "Lancet", Volume 2, pages 850-851, 1955 ("Vallence, 1955")

Webb, N. J., and Pritt, W. R., the article entitled "*Eucalyptus* oil poisoning in childhood: 41 cases in south-east Queensland", in the journal called "Journal of Paediatrics and Child Health", Volume 29, pages 368-371, 1993 ("Webb and Pritt, 1993")

Weinstein, A. M., the book entitled "Asthma, The Complete Guide to Self-Management of Asthma and Allergies for Patients and Their Families", A Fawcett Crest Book, The Ballantine Publishing Group, New York, N.Y., 1988 ("Weinstein, 1988") [Allen M. Weinstein, M.D.]

Williams, D. G., the article entitled "New Uses for An Age-Old Therapy", in the newsletter called "Alternatives For the Health Conscious Individual", Vol. 8, No. 4, October, 1999 ("Williams, 1999") [Dr. David G. Williams]

Again, entire copies of all the above cited references in this section entitled "References" are incorporated herein by reference. In addition, each above cited references refer to yet other papers, publications, books, etc., and entire copies of each and every such document is also incorporated herein by reference in their entirety. For example, Hedges and Wilkens, 1991, cite under its "References" and item "1." a book that is entitled "The Essential Oils", Vol. I, II, and IV, by the author of E. Gunther, Lancaster Press, Lancaster, Pa., 1948, and according the previous sentence, an entire copy of that reference is incorporated herein by this statement.

While the above description contains many specificities, these should not be construed as limitations on the scope of the invention, but rather as exemplification of preferred embodiments thereto. As have been briefly described, there are many possible variations. Accordingly, the scope of the invention should be determined not only by the embodiments illustrated, but by the appended claims and their legal equivalents.

What is claimed is:

1. A method of reducing the incidence of chemotherapy induced nausea in a patient during a chemotherapy session for human cancers comprising at least the following steps:

(a) in a first time period of 10 minutes in advance of a chemotherapy session, before nausea has developed, requiring the patient to inhale an effective amount of vapors of an essential oil of *Mentha piperita* from a hand-held apparatus; and (b) in a second time period, requiring the patient to inhale an effective amount of vapors of an essential oil of *Mentha piperita* every 15 minutes, until the chemotherapy session has ended.

2. The method in claim 1 wherein the effective amount of the vapors from the essential oil from *Mentha piperita* is equal to 11 micrograms of vaporized essential oil.

* * * * *